United States Patent
Kim et al.

(10) Patent No.: US 9,762,227 B2
(45) Date of Patent: Sep. 12, 2017

(54) APPARATUS AND METHOD FOR PROCESSING SIGNAL

(71) Applicants: Samsung Electronics Co., Ltd., Suwon-si (KR); The Industry & Academic Cooperation in Chungnam National University (IAC), Daejeon (KR)

(72) Inventors: Jong Pal Kim, Seoul (KR); Hyoung Ho Ko, Daejeon (KR); Tak Hyung Lee, Suwon-si (KR)

(73) Assignees: Samsung Electronics Co., Ltd., Suwon-si (KR); THE INDUSTRY & ACADEMIC COOPERATION IN CHUNGNAM NATIONAL UNIVERSITY (IAC), Daejeon (KR)

( * ) Notice: Subject to any disclaimer, the term of this patent is extended or adjusted under 35 U.S.C. 154(b) by 25 days.

(21) Appl. No.: 14/614,072

(22) Filed: Feb. 4, 2015

(65) Prior Publication Data
US 2016/0028388 A1     Jan. 28, 2016

(30) Foreign Application Priority Data
Jul. 28, 2014   (KR) .................. 10-2014-0095734

(51) Int. Cl.
*H04B 1/38*     (2015.01)
*H04L 27/04*    (2006.01)
(Continued)

(52) U.S. Cl.
CPC ............... *H03K 7/06* (2013.01); *A61B 5/053* (2013.01); *A61B 5/0531* (2013.01);
(Continued)

(58) Field of Classification Search
CPC ........ H03K 7/06; A61B 5/053; A61B 5/0531; A61B 5/0537; A61B 5/0809;
(Continued)

(56) References Cited

U.S. PATENT DOCUMENTS

| | | | |
|---|---|---|---|
| 7,212,798 B1 * | 5/2007 | Adams | ................ H03G 3/3068 330/278 |
| 7,391,257 B1 | 6/2008 | Denison et al. | |

(Continued)

FOREIGN PATENT DOCUMENTS

| | | |
|---|---|---|
| DE | 10 2011 002 413 A1 | 7/2012 |
| EP | 2 294 979 A1 | 3/2011 |

(Continued)

OTHER PUBLICATIONS

Kassanos, Panagiotis, et al. "An integrated analog readout for multi-frequency bioimpedance measurements." Sensor Journal, IEEE 14.8 (2014) XP055223711: 2792-2800.

(Continued)

*Primary Examiner* — Brandon S Cole
(74) *Attorney, Agent, or Firm* — NSIP Law

(57) ABSTRACT

An apparatus of processing a signal or a biosignal, and a method of processing a signal or a biosignal are provided. The method of processing signal involves receiving a first reference signal having a frequency component of a measurement signal to be applied to a subject, receiving a second reference signal having a frequency component within a frequency bandwidth of an amplifier, and converting a first signal measured from the subject to a second signal within the frequency bandwidth of the amplifier, based on the first reference signal and the second reference signal.

26 Claims, 22 Drawing Sheets

(51) Int. Cl.
- *H03K 7/06* (2006.01)
- *A61B 5/053* (2006.01)
- *H03F 1/02* (2006.01)
- *A61B 5/00* (2006.01)
- *A61B 5/08* (2006.01)
- *H03F 3/00* (2006.01)

(52) U.S. Cl.
CPC .......... *A61B 5/0537* (2013.01); *A61B 5/0809* (2013.01); *A61B 5/7225* (2013.01); *A61B 5/7228* (2013.01); *H03F 1/02* (2013.01); *H03F 3/00* (2013.01); *H03F 2200/261* (2013.01)

(58) Field of Classification Search
CPC ....... A61B 5/7225; A61B 5/7228; H03F 1/02; H03F 3/00; H03F 2200/261
USPC .................................................. 455/230–268
See application file for complete search history.

(56) References Cited

U.S. PATENT DOCUMENTS

| | | | | |
|---|---|---|---|---|
| 2001/0050630 | A1* | 12/2001 | Fujii | G01S 19/03 342/357.64 |
| 2003/0022626 | A1* | 1/2003 | Miquel | H04B 7/15585 455/24 |
| 2008/0269630 | A1 | 10/2008 | Denison et al. | |
| 2009/0124213 | A1* | 5/2009 | Rubin | H04B 1/406 455/76 |
| 2009/0253960 | A1* | 10/2009 | Takenaka | A61B 1/00016 600/118 |
| 2011/0066054 | A1* | 3/2011 | Yazicioglu | A61B 5/04 600/509 |
| 2011/0260898 | A1* | 10/2011 | Velazquez | H03F 1/3247 341/110 |
| 2014/0064339 | A1* | 3/2014 | Kim | H04L 5/0051 375/219 |
| 2016/0128072 | A1* | 5/2016 | Rajagopal | H04W 72/082 370/329 |
| 2016/0274060 | A1* | 9/2016 | Denenberg | G01N 27/9046 |

FOREIGN PATENT DOCUMENTS

| | | |
|---|---|---|
| KR | 10-1010501 B1 | 1/2011 |
| KR | 10-1114674 B1 | 5/2012 |
| KR | 10-1324560 B1 | 11/2013 |
| KR | 10-1324704 B1 | 11/2013 |

OTHER PUBLICATIONS

Extended European Search Report issued Nov. 23, 2015 in counterpart European Application No. EP 15177011.2 (8 pages).

* cited by examiner

APPARATUS AND METHOD FOR PROCESSING SIGNAL

CROSS-REFERENCE TO RELATED APPLICATION(S)

This application claims the benefit under 35 USC 119(a) of Korean Patent Application No. 10-2014-0095734, filed on Jul. 28, 2014, in the Korean Intellectual Property Office, the entire disclosure of which is incorporated herein by reference for all purposes.

BACKGROUND

1. Field

The following description relates to technology for processing an electrical signal and to technology for measuring and processing a biosignal.

2. Description of Related Art

An instrumentation amplifier (IA) is used to measure various signals. For example, an IA may be used in amplifying biosignals such as electrocardiogram (ECG) signals, electromyogram (EMG) signals, photoplethysmogram (PPG) signals, volumetric resistance signals, or motion signals. In general, an IA may comprise a differential amplifier indicating a low offset, low noise, a high common mode rejection, a high loop gain, and high input resistance.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method of processing signal involves receiving a first reference signal having a frequency component of a measurement signal to be applied to a subject, receiving a second reference signal having a frequency component within a frequency bandwidth of an amplifier, and converting a first signal measured from the subject to a second signal within the frequency bandwidth of the amplifier, based on the first reference signal and the second reference signal.

The converting may involve generating a first control signal by combining the first reference signal and the second reference signal, and converting the first signal to the second signal based on the first control signal.

The generating may involve generating the first control signal by performing an XNOR logic operation on the first reference signal and the second reference signal.

The first control signal may have a first time width and a second time width in which a signal amplitude is greater than an upper threshold value, and may have a third time width and a fourth time width in which the signal amplitude is less than a lower threshold value.

The first time width may be equal to the fourth time width, and the second time width is equal to the third time width.

The general aspect of the method may further involve generating a third signal by amplifying the second signal using the amplifier, and converting the third signal to a fourth signal of a baseband.

The converting of the third signal to the fourth signal may involve converting the third signal to the fourth signal based on a second control signal having a frequency component equal to the frequency component of the second reference signal.

The converting of the third signal to the fourth signal may involve converting the third signal to the fourth signal based on a second control signal acquired by phase-shifting the second reference signal by 90 degrees.

The first signal may have a frequency component outside the range of the frequency bandwidth of the amplifier, and the second signal may have an intermediate frequency component within a frequency bandwidth range of the amplifier.

In another general aspect, a method of processing signal involves selecting a single first reference signal from among a plurality of first reference signals based on a measurement mode, generating a first control signal based on the selected first reference signal and a second reference signal having a frequency component within a frequency bandwidth of an amplifier, and converting a first signal measured from a subject to a second signal within the frequency bandwidth of the amplifier, based on the first control signal.

The selecting may involve selecting a first reference signal having a frequency component of a measurement signal to be applied to the subject in a first measurement mode, and selecting a first reference signal having a fixed signal level over time in a second measurement mode.

The first measurement mode may be a mode for measuring bio-impedance information, and the second measurement mode may be a mode for measuring biopotential information.

The generating may involve generating the first control signal by performing an XNOR logic operation on the first reference signal and the second reference signal.

The first control signal may have a first time width and a second time width in which a signal amplitude is greater than an upper threshold value, and may have a third time width and a fourth time width in which the signal amplitude is less than a lower threshold value.

The general aspect of the method may further involve generating a third signal by amplifying the second signal using the amplifier, and converting the third signal to a fourth signal of a baseband.

In another general aspect, a method of processing biosignal may involve converting a frequency component of a biosignal outside a frequency bandwidth of an amplifier to a frequency component within the frequency bandwidth of the amplifier, and amplifying the biosignal having the frequency component converted.

The converted frequency component of the biosignal may be less than a frequency component of a biosignal measured from a subject.

The converted frequency component of the biosignal may be greater than a frequency component of a biosignal measured from a subject.

The converted frequency component of the biosignal may be greater than a frequency component of a baseband signal.

The general aspect of the method may further involve converting the amplified biosignal to a signal of a baseband.

In another general aspect, a signal processing apparatus may include a controller configured to generate a first control signal based on a first reference signal having a frequency component of a measurement signal and a second reference signal having a predetermined frequency component within a frequency bandwidth of an amplifier, a first converter configured to convert a first signal to a second signal having a frequency component within the frequency bandwidth of the amplifier, based on the first control signal, the amplifier configured to output a third signal by amplifying the second signal, and a second converter configured to convert the third signal to a fourth signal of a baseband.

The controller may be configured to generate the first control signal by performing an XNOR logic operation on the first reference signal and the second reference signal.

The first control signal may have a first time width and a second time width in which a signal amplitude may be greater than an upper threshold value, and may have a third time width and a fourth time width in which the signal amplitude may be less than a lower threshold value.

The second converter may be configured to convert the third signal to the fourth signal based on a second control signal having a frequency component equal to the frequency component of the second reference signal.

The second converter may be configured to convert the third signal to the fourth signal based on a second control signal acquired by phase-shifting the second reference signal by 90 degrees.

The signal processing apparatus may be comprised in and may operate within a wearable device.

In another general aspect, a biosignal processing apparatus includes a first converter configured to convert a frequency component of a biosignal outside a frequency bandwidth of an amplifier to a frequency component within the frequency bandwidth of the amplifier, and the amplifier configured to amplify the biosignal having the frequency component converted.

The converted frequency component of the biosignal may be less than a frequency component of a biosignal measured from a subject.

The converted frequency component of the biosignal may be greater than a frequency component of a biosignal measured from a subject.

The converted frequency component of the biosignal may be greater than a frequency component of a baseband signal.

The general aspect of the biosignal processing apparatus may further include a second converter configured to convert the amplified biosignal to a signal of a baseband.

The biosignal processing apparatus may further include a controller configured to generate a first control signal based on a first reference signal having a frequency component of a measurement signal and a second reference signal having a predetermined frequency component comprised in the frequency bandwidth of the amplifier, and the controller may be configured to generate the first control signal by performing an XNOR logic operation on the first reference signal and the second reference signal.

The first control signal may have a first time width and a second time width in which a signal amplitude is greater than an upper threshold value, and may have a third time width and a fourth time width in which the signal amplitude is less than a lower threshold value.

In another general aspect, an apparatus includes an interface configured to transmit a measurement signal to a subject and to receive a reaction signal from the subject; a first converter configured to, in response to a frequency component of a first signal based on the received reaction signal being outside of a frequency bandwidth of an amplifier, convert the first signal to a second signal having a frequency component within the frequency bandwidth of the amplifier; and the amplifier configured to amplify the second signal.

The general aspect of the apparatus may further include a controller configured to generate a first control signal based on a first reference signal having a frequency component of the measurement signal and a second reference signal having a frequency component within the frequency bandwidth of the amplifier, the first converter being configured to convert the first signal to the second signal based on the first control signal.

The controller may be configured to generate the first control signal by performing an XNOR logic operation on the first reference signal and the second reference signal.

Other features and aspects will be apparent from the following detailed description, the drawings, and the claims.

Figure 1:
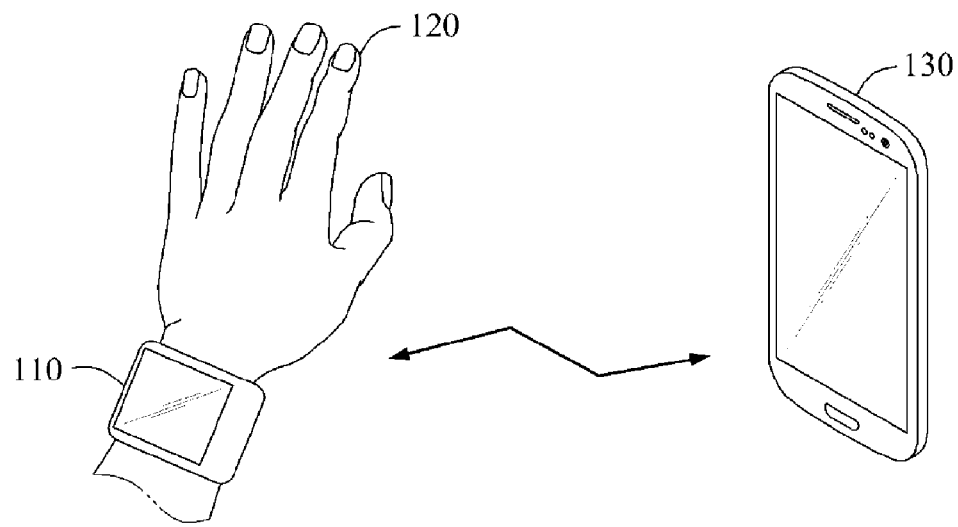
FIG. 1 is a diagram illustrating an example of a biosignal processing apparatus that is applied to a wearable device.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein.

However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, examples will be described with reference to the accompanying drawings. The following structural through functional descriptions are provided to describe the examples and thus, the scope of claims should not be understood to be limited by the examples described herein. Like reference numerals illustrated in the drawings refer to like reference constituent elements through and known functions and structure are omitted here.

FIG. 1 illustrates an example of a biosignal processing apparatus 110. In this example, the biosignal processing apparatus 110 is applied to a wearable device.

The biosignal processing apparatus 110 measures a biosignal and processes the measured biosignal. For example, the biosignal processing apparatus 110 may measure, from a body 120 of a user, bio-impedance information, body component information of the user, and a biosignal such as an electromyogram (EMG) signal, an electrocardiogram (ECG) signal, and a photoplethysmogram (PPG) signal, and may process the measured biosignal. The biosignal may be used to monitor a health state of the user or an emotional state of the user.

In an example, the biosignal processing apparatus 110 may be applied to a variety of application fields such as detecting a biosignal such as body fat by measuring and processing bio-impedance in a mobile environment. The biosignal processing apparatus 110 may be included in a wearable device that is mounted to a user body and operates. For example, the biosignal processing apparatus 110 may be included in a wearable device in a form of a watch, a glove, clothes, a hat, glasses, or shoes, and operate therein. The biosignal processing apparatus 110 may process the biosignal measured from the body 120 to be in a suitable form, and may transmit the processed biosignal to a mobile device 130. The mobile device 130 may analyze the biosignal received from the biosignal processing apparatus 110, and may determine a physical state, a health state, or an emotional state of the user based on the analysis result.

In one example, the biosignal processing apparatus 110 generates a measurement signal, and applies the generated measurement signal to the body 120 through an interface (not shown). For example, the interface may be a bio-electrode configured to measure a biosignal from a subject for measurement, such as the body 120 of the user. In the wearable device, the interface may be attached to the body 120 in a contact or non-contact manner, and may measure a biosignal of the user based on a measurement signal output from the biosignal processing apparatus 110. For example, the interface may measure a biosignal in direct connect with the skin of the body 120, or may measure a biosignal at a distance separate from the skin of the body 120 by at least a predetermined distance. The interface may include a plurality of electrodes configured to measure a biosignal, or sensors such as a light emitting diode (LED), a photodiode, and an optical detector.

The biosignal processing apparatus 110 amplifies the biosignal output from the interface. For example, the biosignal processing apparatus 110 may amplify the biosignal transferred from the interface, using an instrumentation amplifier (IA). According to one example, bio-impedance information of the body 120 may be extracted by applying current to the body 120 as a measurement signal, and by measuring a voltage as a reaction signal. In another example, bio-impedance information of the body 120 may be extracted by applying a voltage to the body 120 and by measuring current as a reaction signal of the applied voltage.

In general, to amplify a biosignal in an accurate manner, a frequency component of a signal input to an amplifier (not shown) of the biosignal processing apparatus 110 needs to be included within an amplifiable frequency bandwidth of the amplifier. For example, in response to a frequency component of a biosignal input to the amplifier being 1 MHz, the amplifier may correctly amplify a biosignal having a frequency bandwidth of at least 1 MHz. Accordingly, in the event that a biosignal input to the amplifier has a relatively high frequency, a frequency bandwidth of the amplifier may have to be accordingly widened so that the amplifier may correctly amplify the biosignal. However, the amount of power used by an amplifier increases in proportion to an increase in the frequency bandwidth of the amplifier.

Thus, according to one example, in the event that a biosignal input to the amplifier has a frequency component beyond the amplifiable frequency bandwidth of the amplifier, the biosignal processing apparatus 110 may modulate the biosignal so that the frequency component of the biosignal may be included in the amplifiable frequency bandwidth of the amplifier. After the modulation, the biosignal processing apparatus 110 may amplify the biosignal using the amplifier and may demodulate the amplified biosignal.

A frequency bandwidth in which the amplifier normally amplifies a biosignal may include a frequency component of a modulated biosignal, not an original biosignal. Accordingly, the biosignal processing apparatus 110 may amplify the biosignal using the amplifier having a frequency bandwidth less than a center frequency of a measurement signal. Since the amplifier having a relatively narrow frequency bandwidth is used, an amount of power used by the amplifier may be reduced. Also, in general, the number of transistors constituting the amplifier is to increase in order to increase the frequency bandwidth of the amplifier. Thus, the biosignal processing apparatus 110 may reduce a design area of the biosignal processing apparatus 110 using the amplifier having the relatively narrow frequency bandwidth.

In an example, the biosignal processing apparatus 110 may operate in various measurement modes. For example, the biosignal processing apparatus 110 may operate in a measurement mode for measuring bio-impedance information or a measurement mode for measuring biopotential information such as ECG or EMG of the user. The biosignal processing apparatus 110 may control a circuit operation based on a control signal to measure all of the bio-impedance information and the biopotential information in the same circuit configuration.

Figure 2:
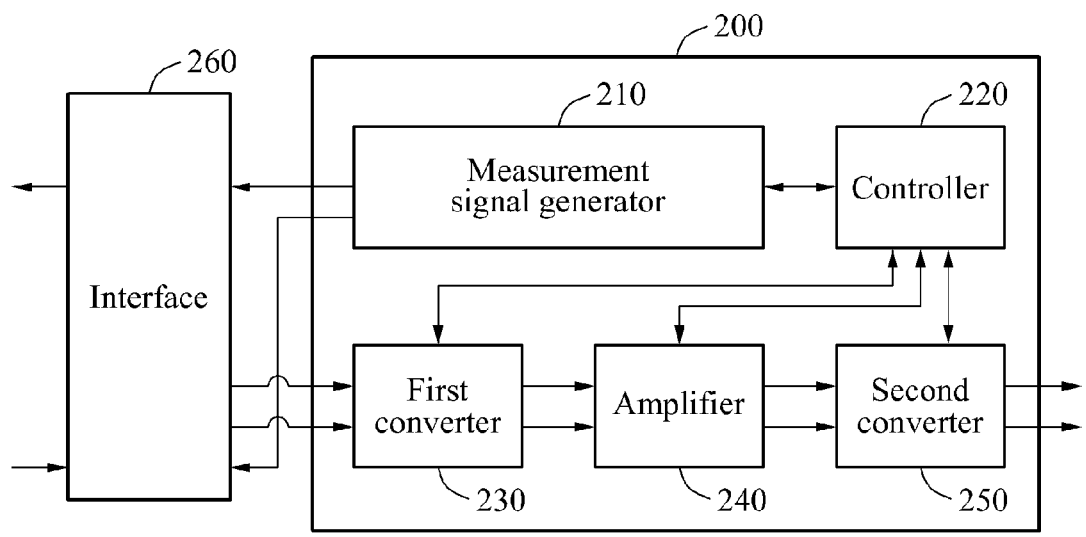
FIG. 2 is a diagram illustrating an operation of an example of a biosignal processing apparatus.

FIG. 2 illustrates an example of a biosignal processing apparatus 200. Referring to FIG. 2, the biosignal processing apparatus 200 includes a measurement signal generator 210, a controller 220, a first converter 230, an amplifier 240, and a second converter 250.

The biosignal processing apparatus 200 operates in one of a plurality of measurement modes available for the biosignal processing apparatus 200. In an example, the biosignal processing apparatus 200 may operate in one of a first measurement mode, a second measurement mode, a third measurement mode, and a fourth measurement mode. The biosignal processing apparatus 200 may measure bio-impedance information in the first measurement mode, the third measurement mode, and the fourth measurement mode, and may measure biopotential information in the second measurement mode. In each of the first measurement mode, the third measurement mode, and the fourth measurement mode, the biosignal processing apparatus 200 may process a biosignal by applying a different method based on a type of bio-impedance desired to be measured and a signal characteristic.

The controller 220 controls the measurement signal generator 210, the first converter 230, the amplifier 240, and the second converter 250 based on the control signal. The controller 220 generates a first control signal for controlling the first converter 230 based on a measurement mode of the biosignal processing apparatus 200.

The controller 220 generates the first control signal using at least one of a static signal such as high and low based on a measurement mode, a signal having a frequency component of a measurement signal or a frequency component of a control signal for controlling the measurement signal generator 210, a second reference signal having a predetermined frequency component included in an amplifiable frequency bandwidth of the amplifier 240, a phase-shifted signal of the second reference signal, a second control signal for controlling the second converter 250, and a phase-shifted signal of the second control signal. In an example, the second reference signal may have a frequency component that is included in the amplifiable frequency bandwidth of the amplifier 240 and is greater than a low noise frequency band of the amplifier 240. The controller 220 may generate the first control signal using only one signal of the aforementioned signals or by combining a plurality of signals.

In an example, a first reference signal may correspond to the control signal for controlling the measurement signal generator 210, and the second reference signal may correspond to the second control signal for controlling the second converter 250. In another example, the first reference signal may correspond to the control signal for controlling the measurement signal generator 210, and the second reference signal may correspond to the phase-shifted signal of the second control signal for controlling the second converter 250.

The controller 220 selects the first reference signal to be used to generate the first control signal based on a measurement mode of the biosignal processing apparatus 200. For example, the controller 220 may select a signal having a frequency component of the measurement signal as the first reference signal in the first measurement mode, and may select a signal having a fixed signal level over time as the first reference signal in the second measurement mode.

Hereinafter, an example of a method of operating the biosignal processing apparatus 200 in the first measurement mode will be described.

In the first measurement mode for measuring bio-impedance information, the measurement signal generator 210 generates a measurement signal for measuring a biosignal. For example, the measurement signal generator 210 may generate alternating current (AC) or AC voltage having a predetermined frequency component, and may transfer the generated AC or AC voltage to an interface 260. The interface 260 applies the measurement signal transferred from the measurement signal generator 210, to a subject through an electrode. For example, the interface 260 may be a bio-electrode configured to measure a biosignal from the subject for measurement, such as a user's body.

The measurement signal generator 210 generates a measurement signal having various frequency components according to a control of the controller 220. The frequency component of the measurement signal may vary based on the subject. The controller 220 determines a frequency component of the measurement signal corresponding to the subject, and controls the measurement signal generator 210 to generate the measurement signal having the frequency component. For example, the controller 220 may control the measurement signal generator 210 to generate a measurement signal having a frequency component of 50 kHz, in order to measure a body fat of a user.

A biosignal generated by the measurement signal generator 210 is applied to the subject through the interface 260 as a measurement signal, and the biosignal is measured as a reaction signal to the measurement signal. For example, the interface 260 may include an anode electrode terminal and a cathode electrode terminal. A potential difference may occur between the anode electrode terminal and the cathode electrode terminal due to the measurement signal flowing in the subject. For example, when the measurement signal is AC having a predetermined center frequency component, a voltage difference between two electrode terminals of the interface 260 may be an AC voltage having the center frequency component of the measurement signal.

In another example, the measurement signal generator 210 may generate a measurement signal in a signal form of a square wave or a sine wave. The measurement signal generator 210 may generate a sine wave using a method such as a Wien's bridge oscillator. For instance, in the event that the first converter 230 or the second converter 250 requires a clock-form signal, the measurement signal generator 210 generates the clock-form signal by making the sine wave pass a comparator (not shown). Alternatively, the measurement signal generator 210 generates a sine wave from data stored in a lookup table using a digital-to-analog (D/A) converter and an analog filter. The measurement signal generator 210 generates the clock-form signal based on an amplitude of the sine wave and viewpoint related information. The generated clock-form signal is used for the first converter 230 or the second converter 250.

For example, when AC flows into the body of a user, charges may collect along a cell membrane while the current passes through the cell membrane. In this example, the cell membrane may function as a capacitor, and an electrical characteristic of the user body may be modeled using the capacitor formed by the cell membrane. Transmittance of electricity with respect to the user body may vary based on a frequency component of AC or AC voltage used as a measurement signal. A variety of body component information of the user may be measured using the characteristic. For example, when the AC is applied to a measurement portion, a voltage drop may occur in the measurement portion due to a bio-impedance. Bio-impedance information may be measured by measuring a potential difference that occurs due to the voltage drop.

The controller 220 generates the first control signal based on the first reference signal having the frequency component of the measurement signal and the second reference signal having the predetermined frequency component included in the frequency bandwidth of the amplifier 240. For example, the controller 220 may generate the first control signal by performing an XNOR logic operation on the first reference signal and the second reference signal. The controller 220 may control the first converter 230 based on the first control signal.

The first converter 230 modulates the frequency component of the biosignal transferred from the interface 260. For example, the first converter 230 may modulate the biosignal so that the frequency component of the biosignal not included in the frequency bandwidth of the amplifier 240 may be included in the frequency bandwidth of the amplifier 240 based on the first control signal output from the controller 220. In the event that the frequency component of the measurement signal or the frequency component of the control signal for controlling the measurement signal generator 210 is outside the frequency bandwidth of the amplifier 240 or approaches the frequency bandwidth of the amplifier 240, the first converter 230 may convert a biosignal to be input to the amplifier 240 to a signal of a frequency band that is included in the amplifiable frequency bandwidth of the amplifier 240 and is greater than a low frequency noise band or a flicker noise area of the amplifier 240.

A biosignal converted by the first converter 230 may have a frequency component less than the frequency component of the measurement signal and greater than a baseband, and may be a signal of an intermediate frequency band included in the amplifiable frequency bandwidth of the amplifier 240. The baseband indicates a frequency band in which a signal corresponding to the original measurement signal is present.

For example, the first converter 230 may modulate a frequency component of a biosignal using a chopper of which a switching operation is controlled based on a control signal. The first converter 230 modulates the frequency component of the biosignal by switching an input/output path of the biosignal transferred from the interface 260 based on a time.

The amplifier 240 amplifies the biosignal of which the frequency component is converted by the first converter 230. The amplifier 240 amplifies the biosignal based on a predetermined gain of the amplifier 240. The frequency component of the biosignal amplified by the amplifier 240 is demodulated by the second converter 250. The second converter 250 converts the biosignal amplified by the amplifier 240 to a signal of the baseband. In an example, the second converter 250 may be included in the amplifier 240 and operate. The second converter 250 may convert the biosignal output from the amplifier 240 to the signal of the baseband using the chopper of which the switching operation is controlled based on the control signal.

The controller 220 generates the second control signal for controlling the second converter 250. The second converter 250 demodulates the biosignal amplified by the amplifier 240 to the signal of the baseband based on the second control signal output from the controller 220. Similar to the second reference signal, the second control signal may have a frequency component that is included in the amplifiable frequency bandwidth of the amplifier 240 and is greater than the low frequency noise band of the amplifier 240. In an example, the second control signal may be a phase-shifted signal of the second reference signal. For example, the second converter 250 may demodulate the amplified biosignal to the signal of the baseband based on the second control signal acquired by phase-shifting the second reference signal by 90 degrees.

When the second control signal having the frequency component equal to the frequency component of the second reference signal is applied to the second converter 250, a real number component is demodulated from the amplified biosignal. When the second control signal that is 90-degree-shifted from the second reference signal is applied to the second converter 250, an imaginary number component is demodulated from the amplified biosignal.

The biosignal processing apparatus 200 filters the signal output from the second converter 250 through a low pass filter, and performs an analog-to-digital (A/D) conversion of the filtered signal. The biosignal processing apparatus 200 may further include a communicator (not shown) configured to transmit the signal converted to a digital form to an outside.

Hereinafter, an example of a method of operating the biosignal processing apparatus 200 in the second measurement mode will be described.

In the second measurement mode for measuring biopotential information, the first converter 230 of the biosignal processing apparatus 200 converts a signal to be input to the amplifier 240 to a signal that is included in the amplifiable frequency bandwidth of the amplifier 240 and is not included in the low frequency noise band of the amplifier 240. The controller 220 outputs the same signal as the second control signal for controlling the second converter 250 or the phase-shifted signal of the second control signal, as the first control signal for controlling the first converter 230.

The controller 220 generates the first control signal by selecting a signal having a fixed signal level over time as the first reference signal, and by performing an XNOR logic operation on the first reference signal and the second reference signal. For example, when the controller 220 performs an XNOR logic operation on a reference voltage signal having a high logic state at all times over time and the second reference signal in the second measurement mode, the first control signal generated through the XNOR logic operation may have the frequency component equal to the frequency component of the second reference signal. The second reference signal may be the same signal as the second control signal or the phase-shifted signal of the second control signal.

In the second measurement mode, a biosignal converted by the first converter 230 may have a frequency component greater than a frequency band of the biosignal before conversion and a baseband, and may be a signal of an intermediate frequency band included in the amplifiable frequency bandwidth of the amplifier 240. There is no need to apply a separate measurement signal to a subject in order to measure a biopotential of the subject. Thus, in the second measurement mode, the measurement signal generator 210 may be inactivated, or an output of the measurement signal generator 210 may be blocked.

The second converter 250 demodulates the biosignal amplified by the amplifier to the signal of the baseband, based on the second control signal output from the controller 220. In an example, the frequency component of the second control signal may be equal to the frequency component of the second reference signal.

Hereinafter, an example of a method of operating the biosignal processing apparatus 200 in the third measurement mode will be described.

In the third measurement mode for measuring bio-impedance information, the biosignal processing apparatus 200 measures bio-impedance information, for example, the moisture content of the skin. To measure the moisture content of the skin, the biosignal processing apparatus 200 applies a measurement signal of a predetermined frequency to the skin and measures a biosignal that is an electrical reaction signal to the measurement signal.

The measurement signal generator 210 generates a measurement signal including a predetermined frequency component, for example, 30 Hz, and the generated measurement signal is applied to a user body through the interface 260. For example, the measurement signal may be a current signal in a square wave form or a sine wave form. Measuring the biosignal corresponding to the reaction signal of the measurement signal from the subject may be performed at a location at which the measurement signal is applied or a location different from the corresponding location. For example, when the biosignal is measured at the location at which the measurement signal is applied, electrical interfacing with the measurement signal may occur at two locations. When the biosignal is measured at the location different from the location at which the measurement signal is applied, electrical interfacing with the subject may occur at four locations.

The measured biosignal includes information desired to be measured from a frequency band based on the predetermined frequency, for example, 30 Hz, of the measurement signal. Information included in the biosignal is sufficiently included in the amplifiable frequency bandwidth of the amplifier 240 and thus, the first converter 230 outputs the biosignal transferred from the interface 260 as is without converting the transferred biosignal. The first control signal for controlling the first converter 230 may be a static signal in a logically high state or low state.

A biosignal amplified by the amplifier 240 is demodulated by the second converter 250. The second control signal provided to the second converter 250 for demodulation may have the same frequency component, for example, 30 Hz as the control signal for controlling the measurement signal generator 210 or the measurement signal generated by the measurement signal generator 210. The controller 220 may use the control signal for controlling the measurement signal generator 210 as is, or may use, as the second control signal, a phase-shifted signal of the control signal for controlling the measurement signal generator 210. When a phase difference is absent between the control signal for controlling the measurement signal generator 210 and the second control signal, a real number component is extracted from the signal input to the second converter 250. When a phase difference of 90 degrees is present between the control signal for controlling the measurement signal generator 210 and the second control signal, an imaginary number component is extracted from the signal input to the second converter 250.

Hereinafter, an example of a method of operating the biosignal processing apparatus 200 in the fourth measurement mode will be described.

In the fourth measurement mode for measuring bio-impedance information, the biosignal processing apparatus 200 measures bio-impedance information, for example, the moisture content of the skin, which is similar to the third measurement mode. To measure the moisture content of the skin, the biosignal processing apparatus 200 applies a measurement signal of a predetermined frequency to the skin and measures a biosignal that is an electrical reaction signal to the measurement signal.

Dissimilar to the third measurement mode, in the fourth measurement mode, the biosignal processing apparatus 200 converts and amplifies the measured biosignal. The measurement signal generator 210 generates a measurement signal including a predetermined frequency component, for example, 30 Hz, and the generated measurement signal is applied to a user body through the interface 260. The biosignal input to the first converter 230 may have a frequency band that uses a predetermined frequency component of the measurement signal as a center frequency, and the frequency band of the biosignal may be included in the low frequency noise band of the amplifier 240, for example, the frequency band within 1 kHz.

To amplify the biosignal by avoiding the low frequency noise band of the amplifier 240, the first converter 230 converts the biosignal to a signal that is included in the amplifiable frequency band of the amplifier 240 and capable of avoiding the low frequency noise band of the amplifier 240. For example, the first converter 230 may modulate the frequency component of the biosignal based on the first control signal having the frequency component of 4 kHz.

A biosignal frequency-modulated by the first converter 230 is amplified by the amplifier 240. The biosignal amplified by the amplifier 240 is demodulated to the signal of the baseband again by the second converter 250. The second control signal input to the second converter 250 is generated based on the control signal for controlling the measurement signal generator 210 and the first control signal. In an example, the controller 220 may generate the second control signal by performing an XNOR logic operation on the control signal for controlling the measurement signal generator 210 and the first control signal. Also, the controller 220 may generate the second control signal by performing an XNOR logic operation on the first control signal and a phase-shifted signal of the control signal for controlling the measurement signal generator 210.

Figure 3A:
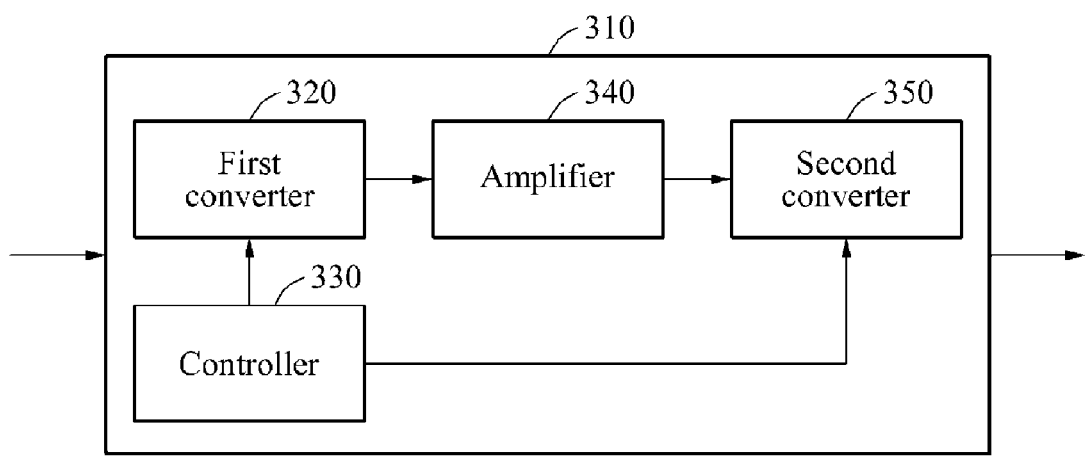
FIG. 3A is a diagram illustrating an example of a signal processing apparatus.

FIG. 3A illustrates an example of a signal processing apparatus 310.

Referring to FIG. 3A, the signal processing apparatus modulates and amplifies a frequency component of an input signal based on a frequency bandwidth of an amplifier, and demodulates the input signal to a signal of a baseband. In an example, the signal processing apparatus 310 may modulate a signal having a high frequency component to a signal of an intermediate frequency band that is included in the frequency bandwidth of the amplifier, may amplify the modulated signal, and may convert the amplified signal to the signal of the baseband. The signal processing apparatus 310 may be included in a wearable device and operate.

Referring to FIG. 3A, the signal processing apparatus 310 includes a first converter 320, a controller 330, an amplifier 340, and a second converter 350.

The controller 330 generates a first control signal for controlling the first converter 320. The controller 330 generates the first control signal based on a first reference signal having a frequency component of a measurement signal and a second reference signal having a predetermined frequency component included in a frequency bandwidth of the amplifier 340. For example, the controller 330 may generate the first control signal by performing an XNOR logic operation on the first reference signal and the second reference signal. The second reference signal may have a frequency component that is included in an amplifiable frequency bandwidth of the amplifier 340 and greater than a low noise frequency band of the amplifier 340.

The first converter 320 converts a first signal to a second signal having a frequency component included in the frequency bandwidth of the amplifier 340 based on the first control signal. The first signal is a signal that is input to the signal processing apparatus 310 as a signal to be signal processed. For example, the first signal may be a biosignal that is measured as a reaction signal to a measurement signal applied to a subject for measurement. The first signal may have a frequency component greater than the frequency bandwidth of the amplifier 340 or corresponding to the frequency bandwidth of the amplifier 340. The second signal output from the first converter 320 may have a frequency component included in the frequency bandwidth of the amplifier 340.

The first converter 320 modulates the first signal to a signal having a frequency component included in the frequency bandwidth of the amplifier 340 and not included in the low frequency noise band of the amplifier 340. The first converter 320 may include, for example, a plurality of switches, and may include a chopper configured to modulate a frequency component of an input signal based on the control signal. The first converter 320 modulates the frequency component of the first signal by controlling a switching operation of the chopper based on the first control signal, and generates the second signal.

Figure 3B:
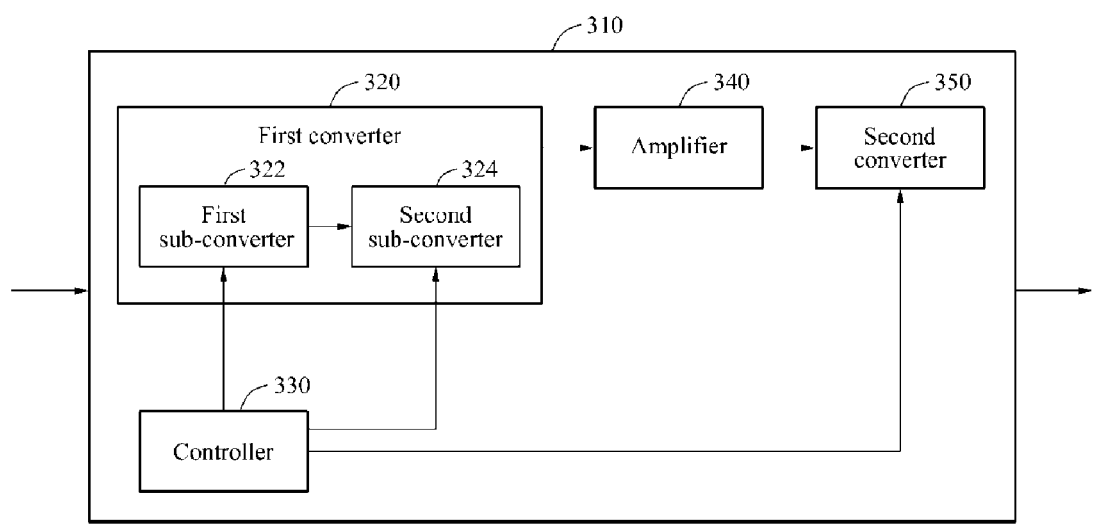
FIG. 3B is a diagram illustrating another example of a signal processing apparatus.

In another example, referring to FIG. 3B, the first converter 320 includes a first sub-converter 322 and a second sub-converter 324. The first sub-converter 322 may be connected to the second sub-converter 324, and the second sub-converter 324 may be connected to the amplifier 340. The first sub-converter 322 converts the first signal to a signal of a baseband. The second sub-converter 324 converts the first signal converted to the signal of the baseband by the first sub-converter 322, to the second signal included in the frequency bandwidth of the amplifier 340.

The controller 330 applies, to the first sub-converter 322, a control signal having a frequency component equal to the frequency component of the measurement signal used to measure the first signal. The controller 330 applies, to the second sub-converter 324, a control signal having a predetermined frequency component included in the frequency bandwidth of the amplifier 340. As described above, control signals output from the controller 330 are sequentially applied to the first sub-converter 322 and the second sub-converter 324, respectively, and the frequency component of the input signal is modulated.

Referring back to FIG. 3A, the amplifier 340 amplifies the second signal transferred from the first converter 320 and outputs a third signal. The second converter 350 converts the third signal to a fourth signal of a baseband. The controller 330 generates a second control signal for controlling the second converter 350, and transfers the generated second control signal to the second converter 350. The second converter 350 modulates a frequency component of the third signal based on the second control signal, and generates the fourth signal having a frequency component of the baseband. For example, the second converter 350 may include a plurality of switches and may include a chopper configured to modulate the frequency component of the input signal based on the control signal. The second converter 350 may convert the third signal to the fourth signal by controlling a switching operation of the chopper to which the third signal is input based on the second control signal.

The controller 330 determines the frequency component of the second control signal based on the frequency component of the second reference signal. The second reference signals used to generate the second control signal and the first control signal may have the same frequency component or may have a phase difference of 90 degrees. The third signal generated by the controller 330 is demodulated by the second converter 350 based on the second control signal generated by the controller 330, and the fourth signal is output from the second converter 350. When the second control signal has the frequency component equal to the frequency component of the second reference signal, the fourth signal output from the second converter 350 includes a real number component. In an example, the second converter 350 may convert the third signal to the fourth signal based on the second control signal acquired by phase-shifting the second reference signal by 90 degrees. When a phase difference of 90 degrees is present between the second control signal and the second reference signal, the fourth signal output from the second converter 350 includes an imaginary number component.

In an example, the signal processing apparatus 310 may operate in one of a first measurement mode, a second measurement mode, a third measurement mode, and a fourth measurement mode. The first measurement mode is a mode for measuring impedance information. The first measurement mode may be executed when the frequency component of the measurement signal used to measure the impedance information is equivalent to or greater than the amplifiable frequency bandwidth of the amplifier 340. The second measurement mode is a mode for measuring biopotential information.

The third measurement mode is a mode for measuring impedance information. The third measurement mode may be executed when the frequency component of the measurement signal used to measure the impedance information is included in the amplifiable frequency bandwidth of the amplifier 340. The fourth measurement mode is a mode for measuring impedance information. The fourth measurement mode may be executed when the frequency component of the measurement signal used to measure the impedance information is included in the amplifiable frequency bandwidth of the amplifier 340, and is included in or equivalent to a low frequency noise band of the amplifier 340.

The controller 330 generates the first control signal for controlling the first converter 320 based on the measurement mode. For example, the controller 330 may generate the first control signal using at least one of a static signal such as high and low based on the measurement signal, a signal having the frequency component of the measurement signal, the second reference signal having the predetermined frequency component included in the amplifiable frequency bandwidth of the amplifier 340, the phase-shifted signal of the second reference signal, the second control signal for controlling the second converter 350, and the phase-shifted signal of the second control signal. The controller 330 may generate the first control signal using only one of the aforementioned signals or by combining a plurality of signals. In an example, the second control signal may have the frequency component equal to the frequency component of the second reference signal.

The controller 330 selects a single signal from among the plurality of signals based on the measurement mode and generates the first control signal based on the selected signal and the second reference signal having the predetermined frequency component included in the frequency bandwidth of the amplifier 340. The controller 330 selects the first reference signal to be used for generating the first control signal based on the measurement mode of the signal processing apparatus 310.

For example, in the first measurement mode, the controller 330 may generate the first control signal by selecting, as the first reference signal, a signal having the frequency component of the measurement signal and by performing an XNOR logic operation on the second reference signal and the signal having the frequency component of the measurement signal. In second measurement mode, the controller 330 may generate the first control signal by selecting, as the first reference signal, a signal having a fixed signal level over time and by performing an XNOR logic operation on the second reference signal and the signal having the fixed signal level over time. The signal having the fixed signal level over time may be a signal having a high logic value at all times regardless of a flow of time. In the first measurement mode and the second measurement mode, the first signal input to the first converter 320 may be modulated so that the frequency component of the first signal may be included in the frequency bandwidth of the amplifier 340. In the second measurement mode, the frequency component of the first signal may be modulated within the range of the frequency bandwidth of the amplifier 340 by the first converter 320.

In the third measurement mode, the first converter 320 outputs the input first signal to the amplifier 340 as is, without converting the first signal. The first control signal for controlling the first converter 320 is a static signal in a logically high state or low state. The first signal amplified by the amplifier 340 is demodulated by the second converter 350. The second control signal provided to the second converter 350 for demodulation has the same frequency component as the measurement signal. Based on a phase of the second control signal, a real number component or an imaginary number component may be extracted from the signal input to the second converter 350.

In the fourth measurement mode, the signal processing apparatus 310 converts and amplifies the input first signal, which differs from the third measurement mode. To amplify the first signal by avoiding the low frequency noise band of the amplifier 340, the first converter 320 converts the first signal to the second signal that is included in the amplifiable frequency band of the amplifier 340 and capable of avoiding the low frequency noise band of the amplifier 340. The second signal is amplified by the amplifier 340 and the third signal corresponding to the amplified second signal is output. The third signal output from the amplifier 340 is demodulated to the signal of the baseband again by the second converter 350.

In an example, the first converter 320, the controller 330, the amplifier 340, and the second converter 350 of FIGS. 3A and 3B may correspond to the first converter 230, the controller 220, the amplifier 240, and the second converter 250 of FIG. 2. Accordingly, a description for the first converter 320, the controller 330, the amplifier 340, and the second converter 350 illustrated in FIGS. 3A and 3B may be found in the description provided with reference to FIG. 2, and vice versus.

FIGS. 4A through 4D illustrate graphs showing an example of a method that may be used to process a signal in a first measurement mode.

Figure 4A:
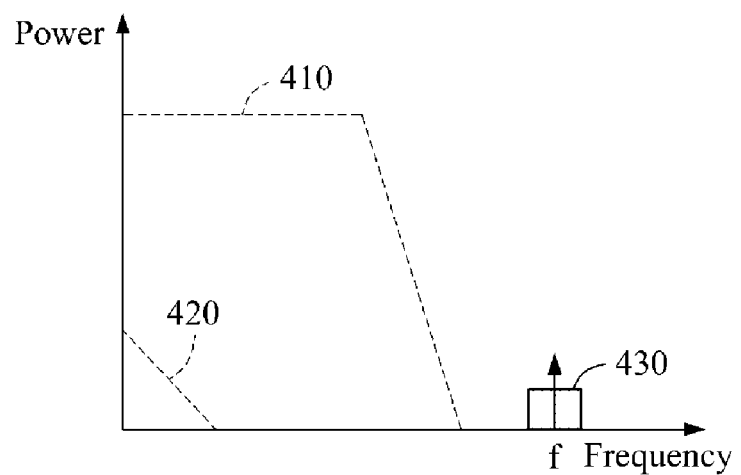
FIGS. 4A through 4D are graphs illustrating an example of a method of processing a signal in a first measurement mode.

FIG. 4A illustrates an example of a first signal 430 input to the first converter 320 in the first measurement mode for measuring bio-impedance information. A frequency component f of the first signal 430 is located outside an amplifiable frequency bandwidth 410 of the amplifier 340. In general, the amplifier 340 accurately amplifies a signal included in the frequency bandwidth 410. Thus, in the event that a first signal 430 that is outside the frequency bandwidth 410 of an amplifier 340 is input to the amplifier 340, the amplifier 340 may not accurately amplify the first signal 430. To accurately amplify the first signal 430 using the amplifier 340, the frequency component f of the first signal 430 needs to be less than a cutoff frequency of the frequency bandwidth 410 of the amplifier 340.

Figure 4B:
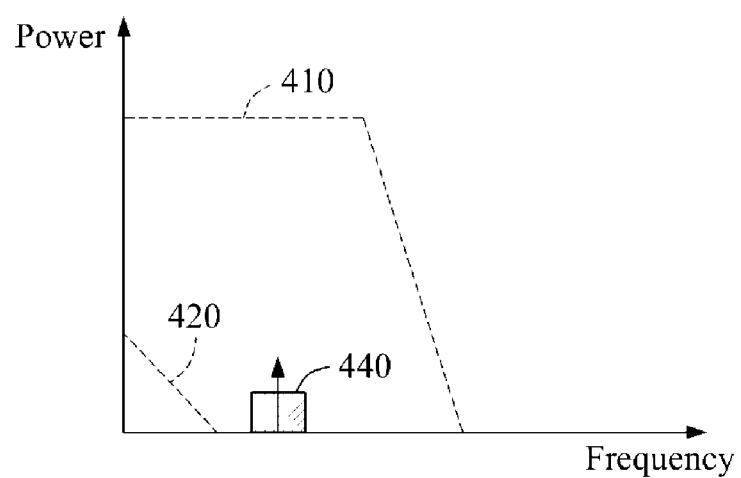

FIG. 4B illustrates an example of a second signal 440 output from the first converter 320. The first converter 320 may modulate a frequency component of the first signal 430 that is outside the bandwidth 410 and may output the second signal 440 having a frequency component included in the frequency bandwidth 410 of the amplifier 340. The first converter 320 may convert the first signal 430 to the second signal 440 having the frequency component included in the frequency bandwidth 410 of the amplifier 340 and greater than a low frequency noise band 420 of the amplifier 340 based on the low frequency noise band 420, without directly converting the first signal 430 to a signal of the baseband.

Figure 4C:
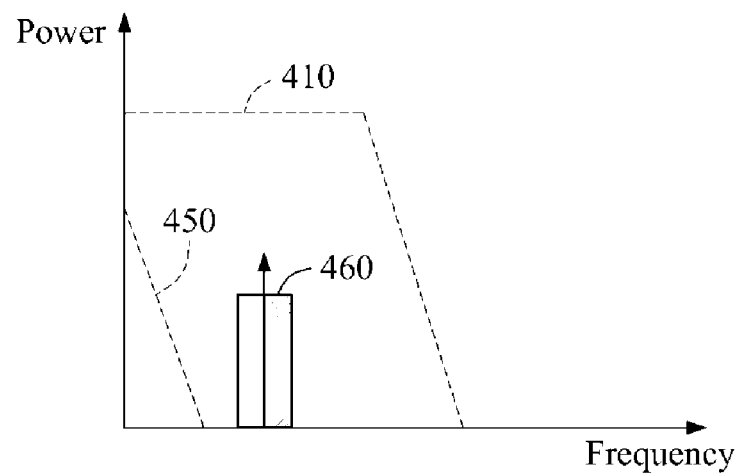

FIG. 4C illustrates an example of a third signal 460 input to the second converter 350. The amplifier 340 generates the third signal 460 by amplifying the second signal 440. By converting the first signal 430 to the second signal 440 having the frequency component outside the low frequency band 420 of the amplifier 340 and by amplifying the second signal 440, noise may be reduced. An area 450 indicates low frequency noise of the amplifier 340 amplified by the amplifier 340.

Figure 4D:
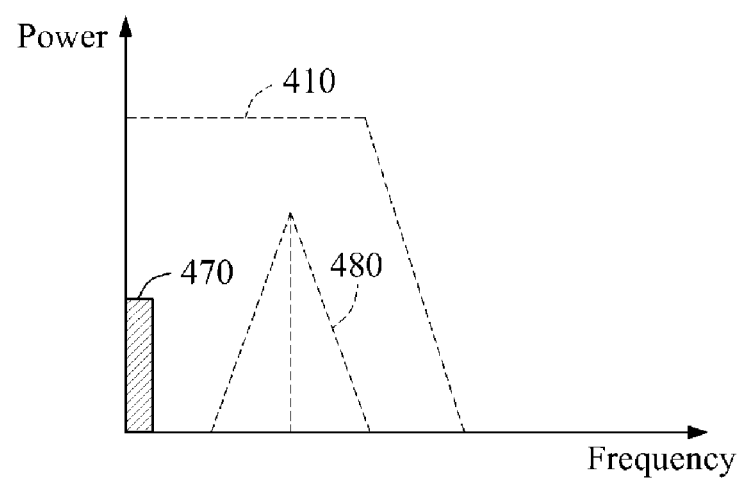

FIG. 4D illustrates an example of a fourth signal 470 output from the second converter 350. The second converter 350 converts the third signal 460 output from the amplifier 340, to a fourth signal 470 having a frequency component of a baseband. The fourth signal 470 converted to the signal of the baseband includes a real number component or an imaginary number component of the first signal 430. An area 480 indicates that the low frequency noise of the amplifier 340 is amplified and then frequency-converted.

Referring to FIGS. 4A through 4D, in the event that a frequency component of an input signal is not included in the amplifiable frequency bandwidth 410 of the amplifier 340, the signal processing apparatus 310 may convert the input signal to a signal included in the frequency bandwidth 410 of the amplifier 340, and may amplify and output the converted signal. Accordingly, with the example of the method of processing a signal illustrated in FIGS. 4A through 4D, it is possible to use an amplifier 340 having a relatively narrow frequency bandwidth in the signal processing apparatus 310 to amplify the signal while allowing an amount of power used by the amplifier 340 to be reduced.

FIGS. 5A through 5D are graphs illustrating an example of a method of processing a signal in a second measurement mode.

Figure 5A:
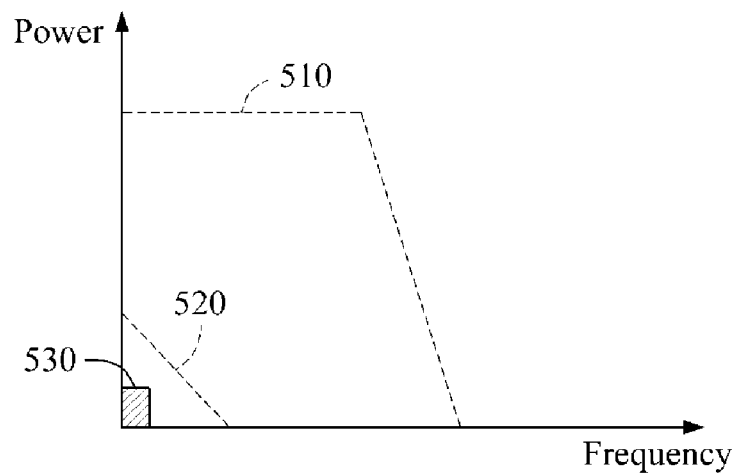
FIGS. 5A through 5D are graphs illustrating an example of a method of processing a signal in a second measurement mode.

FIG. 5A illustrates an example of a first signal 530 input to the first converter 320 in the second measurement mode for measuring biopotential information. A frequency component of the first signal 530 is included in an amplifiable frequency bandwidth 510 of the amplifier 340 and is included in a low frequency noise band 520 of the amplifier 340.

Figure 5B:
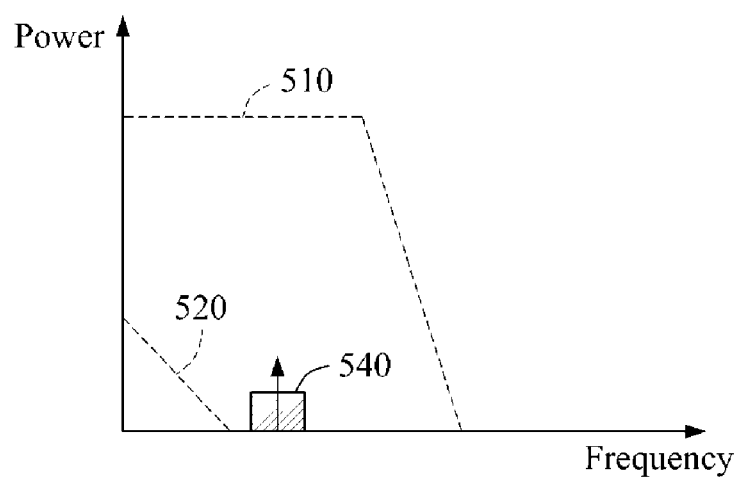

FIG. 5B illustrates an example of a second signal 540 output from the first converter 320. The first converter 320 modulates the frequency component of the first signal 530 and outputs the second signal 540 having a frequency component that is included in the frequency bandwidth 510 of the amplifier 340 and not included in the low frequency noise band 520 of the amplifier 340. The second signal 540 may have the frequency component greater than the frequency component of the first signal 530 and a baseband, and may be a signal of an intermediate frequency band included in the frequency bandwidth 510 of the amplifier 340.

Figure 5C:
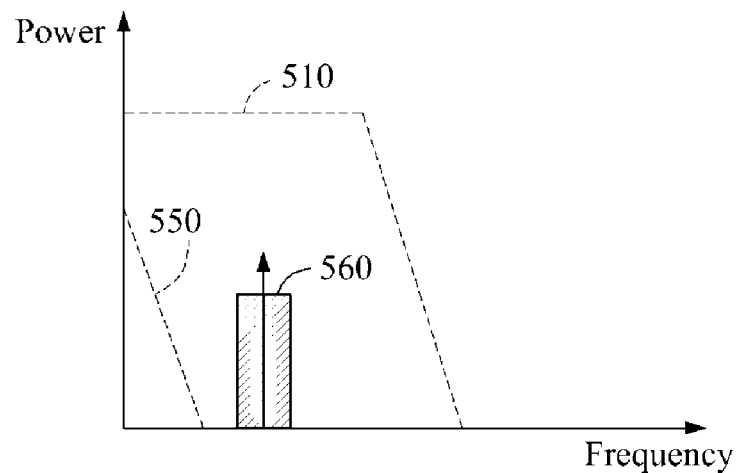

FIG. 5C illustrates an example of a third signal 560 input to the second converter 350. The amplifier 340 amplifies the second signal 540 and outputs the third signal 560. By converting the first signal 530 to the second signal 540 having the frequency component outside the low frequency band 520 of the amplifier 340, noise may be reduced. An area 550 indicates low frequency noise of the amplifier 340 amplified by the amplifier 340.

Figure 5D:
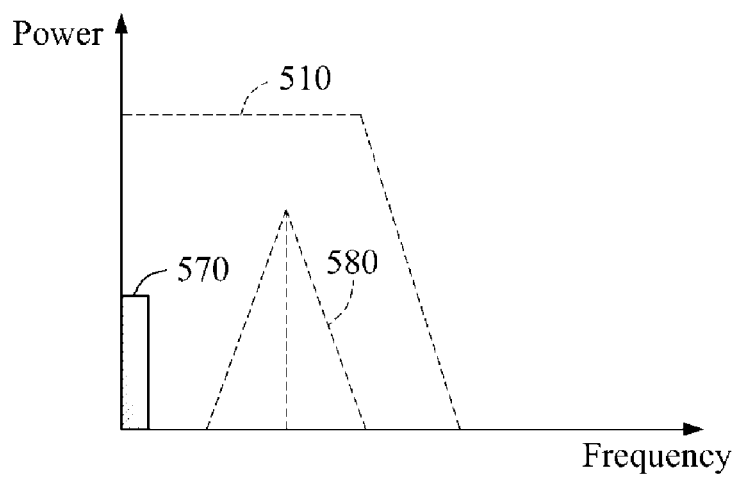

FIG. 5D illustrates an example of a fourth signal 570 output from the second converter 350. The second converter 350 converts the third signal 560 output from the amplifier 340 to the fourth signal 570 having a frequency component of a baseband. The fourth signal 570 converted to the signal of the baseband includes a real number component or an imaginary number component of the first signal 530. An area 580 indicates that the low frequency noise of the amplifier 340 is amplified and then frequency-converted.

Referring to FIGS. 5A through 5D, although a frequency component of an input signal is included in the low frequency noise band 520 of the amplifier 340, the signal processing apparatus 310 may convert the input signal to a signal included in the frequency bandwidth 510 of the amplifier 340 and not included in the low frequency noise band 520 of the amplifier 340, and may amplify and output the converted signal.

FIGS. 6A through 6D illustrate graphs showing an example of a method of processing a signal in a third measurement mode.

Figure 6A:
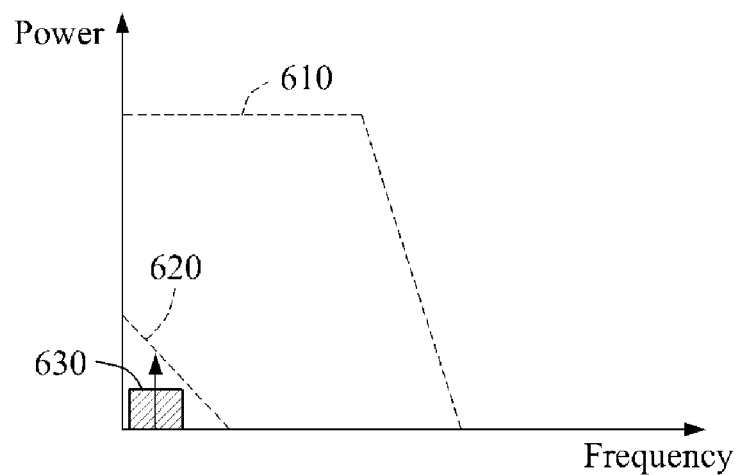
FIGS. 6A through 6D are graphs illustrating an example of a method of processing a signal in a third measurement mode.

FIG. 6A illustrates an example of a first signal 630 input to the first converter 320 in the third measurement mode for measuring bio-impedance information. A frequency component of the first signal 630 is included in an amplifiable frequency bandwidth 610 of the amplifier 340 and is also included in a low frequency band 620 of the amplifier 340.

Figure 6B:
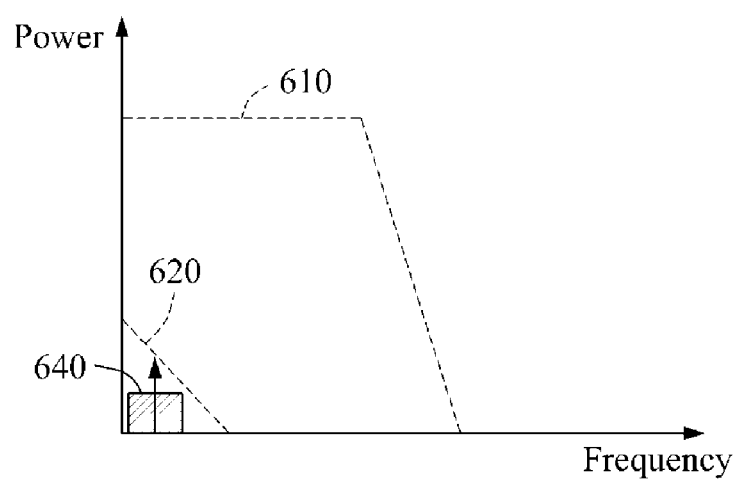

FIG. 6B illustrates an example of a second signal 640 output from the first converter 320. In the third measurement mode, the first converter 320 outputs the input first signal 630 to the amplifier 340 as is as the second signal 640, without converting the first signal 630.

Figure 6C:
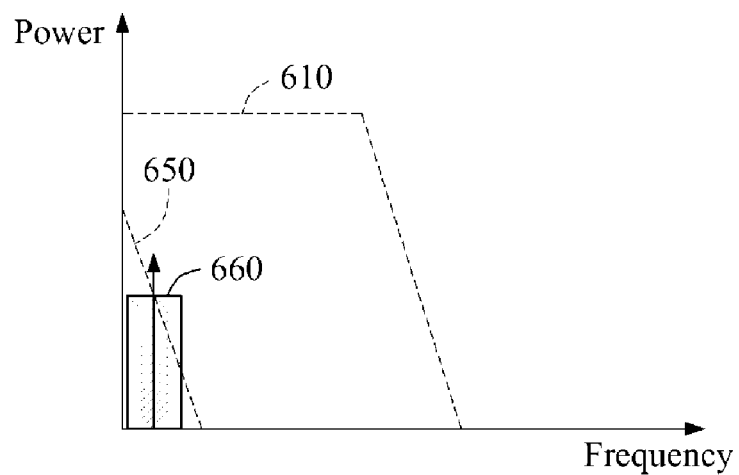

FIG. 6C illustrates an example of a third signal 660 input to the second converter 350. The amplifier 340 amplifies the second signal 640 and outputs the third signal 660. An area 650 indicates low frequency noise of the amplifier 340 amplified by the amplifier 340.

Figure 6D:
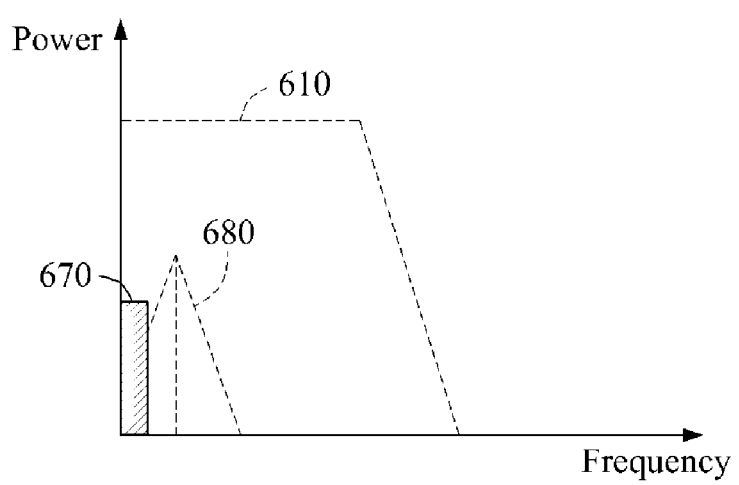

FIG. 6D illustrates an example of a fourth signal 670 output from the second converter 350. The second converter 350 converts the third signal 660 output from the amplifier 340 to the fourth signal 670 having a frequency component of a baseband. The fourth signal 670 converted to the signal of the baseband includes a real number component or an imaginary number component of the first signal 630. An area 680 indicates that the low frequency noise of the amplifier 340 is amplified and then frequency-converted.

FIGS. 7A through 7D illustrate graphs showing an example of a method of processing a signal in a fourth measurement mode.

Figure 7A:
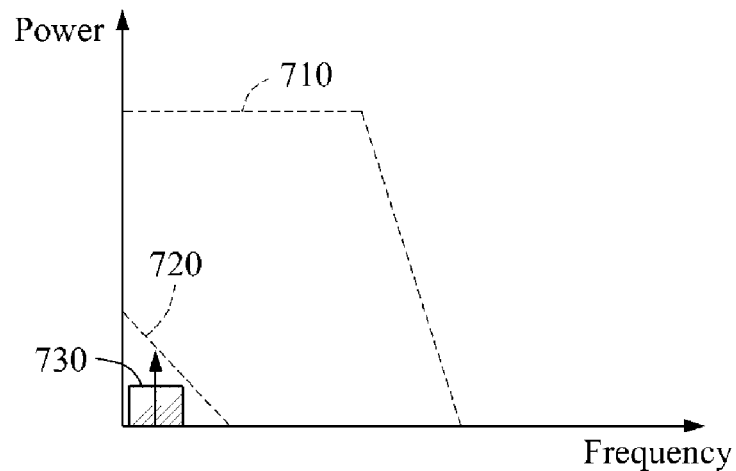
FIGS. 7A through 7D are graphs illustrating an example of a method of processing a signal in a fourth measurement mode.

FIG. 7A illustrates an example of a first signal 730 input to the first converter 320 in the third measurement mode for measuring bio-impedance information. A frequency component of the first signal 730 is included within an amplifiable frequency bandwidth 710 of the amplifier 340 and is also included within a low frequency band 720 of the amplifier 340.

Figure 7B:
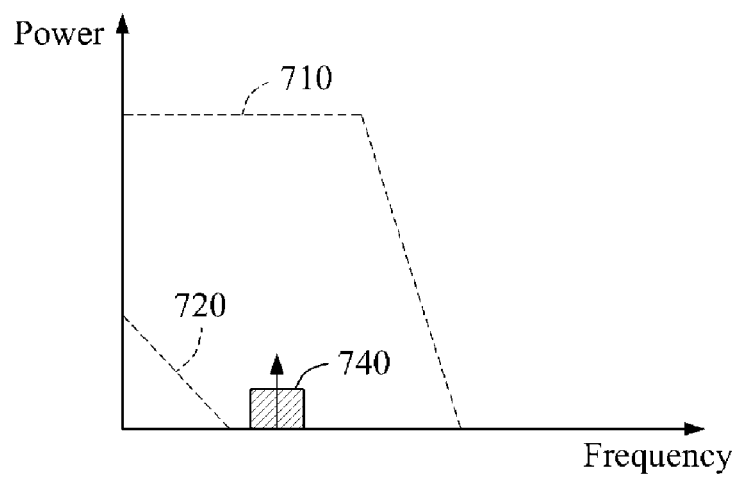

FIG. 7B illustrates an example of a second signal 740 output from the first converter 320. The first converter 320 modulates the frequency component of the first signal 730 and outputs the second signal 740 having a frequency component included in the frequency bandwidth 710 of the amplifier 340 and not included in the low frequency noise band 720 of the amplifier 340. The second signal 740 may have the frequency component greater than the frequency component of the first signal 730 and a baseband, and may be a signal of an intermediate frequency band included within the frequency bandwidth 710 of the amplifier 340 710.

Figure 7C:
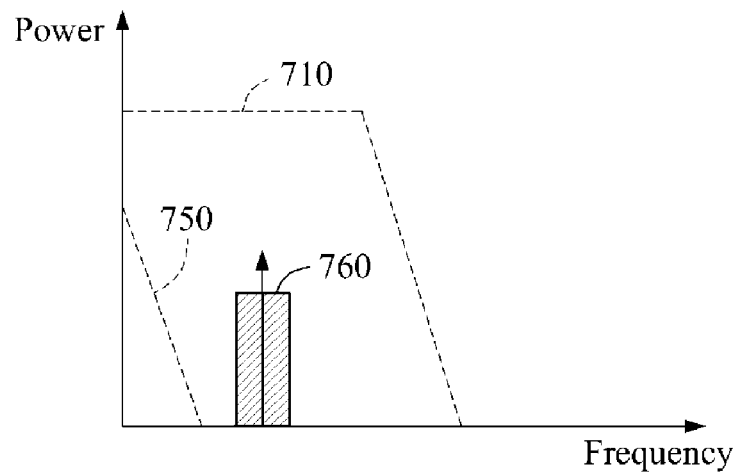

FIG. 7C illustrates an example of a third signal 760 input to the second converter 350. The amplifier 340 amplifies the second signal 740 and outputs the third signal 760. By converting the first signal 730 to the second signal 740 having the frequency component outside the low frequency noise band 720 of the amplifier 340, noise may be reduced. An area 750 indicates low frequency noise of the amplifier 340 amplified by the amplifier 340.

Figure 7D:
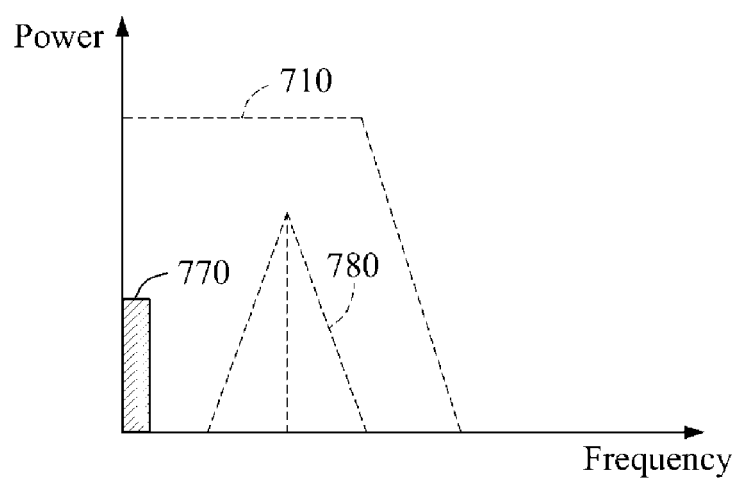

FIG. 7D illustrates an example of a fourth signal 770 output from the second converter 350. The second converter 350 converts the third signal 760 output from the amplifier 340 to the fourth signal 770 having a frequency component of a baseband. The fourth signal 770 converted to the signal of the baseband includes a real number component or an imaginary number component of the first signal 730. An area 780 indicates that the low frequency noise of the amplifier 340 is amplified and then frequency-converted.

Referring to FIGS. 7A through 7D, the signal processing apparatus 310 may convert an input signal to a signal having a frequency component included within the frequency bandwidth 710 of the amplifier 340 and outside of the low frequency noise band 720 of the amplifier 340, and may amplify and output the converted signal.

Hereinafter, an example in which a signal processing apparatus according to example embodiments receives a biosignal as a first signal and processes the received biosignal will be described with reference to FIGS. 8 through 11. However, the scope of rights should not be interpreted to be limited to the example in which the signal processing apparatus processes the biosignal. The signal processing apparatus may process various types of electrical signals.

Figure 8:
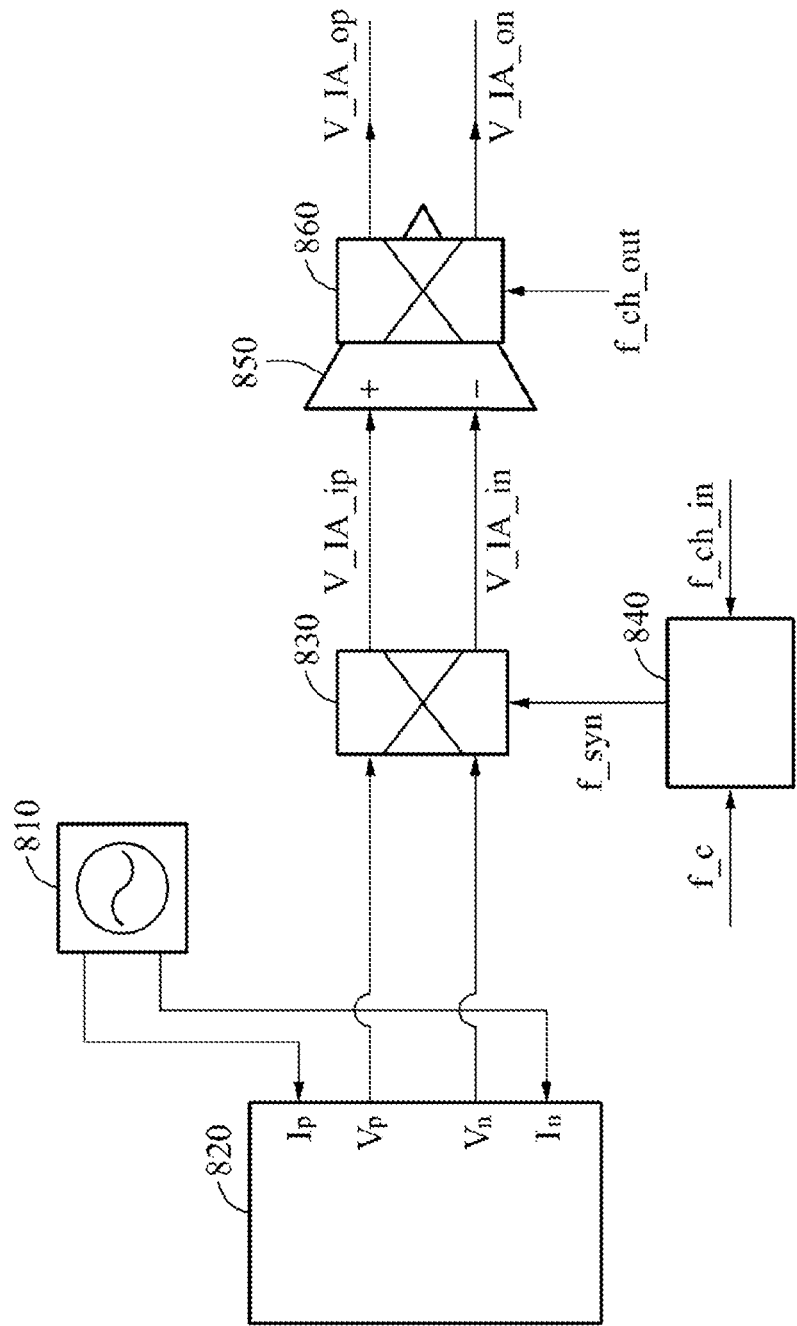
FIG. 8 is a circuit diagram illustrating an example of a signal processing apparatus.

FIG. 8 includes a circuit diagram illustrating an example of a signal processing apparatus. Referring to FIG. 8, the signal processing apparatus includes a first converter 830, a controller 840, an amplifier 850, and a second converter 860. The measurement signal generator 810 may be included in the signal processing apparatus or may operate outside the signal processing apparatus.

The measurement signal generator 810 generates a measurement signal having a predetermined frequency component. For example, the measurement signal generator 810 may generate an AC signal having a frequency component of 1 MHz and may transfer the generated AC signal to an $I_p$ terminal and an $I_n$ terminal of an interface 820. AC signals transferred to the $I_p$ terminal and the $I_n$ terminal of the interface 820 may have a phase difference with respect to each other by 180 degrees. As another example, the measurement signal generator 820 may generate an AC signal having a predetermined frequency component as a measurement signal.

The interface 820 allow the AC transferred from the measurement signal generator 810 to flow into a subject for measurement through the $I_p$ terminal and the $I_n$ terminal. The AC flowing into the subject through the $I_p$ terminal and the $I_n$ terminal of the interface 820 form an AC voltage between a $V_p$ terminal and a $V_n$ terminal of the interface 820. The AC voltage formed between the $V_p$ terminal and the $V_n$ terminal of the interface 820 may have the same frequency component as the AC signal output from the measurement signal generator 810. The interface 820 may transfer, to the first converter 830, biosignals $V_p$ and $V_n$ that are measured in a form of an AC voltage signal.

The controller 840 generates a first control signal f_syn having a synthetic frequency component based on a first reference signal f_c having a frequency component of the measurement signal and a second reference signal f_ch_in having a predetermined frequency component included in a frequency bandwidth of the amplifier 850. For example, the controller 840 may generate the first control signal f_syn by performing an XNOR logic operation on the first reference signal f_c and the second reference signal f_ch_in. The controller 840 may control the first converter 830 based on the first control signal f_syn.

In another example, the signal processing apparatus may operate in a plurality of measurement modes. The controller 840 may generate the first control signal based on a measurement mode of the signal processing apparatus. For example, in a first measurement mode for measuring bio-impedance information, the controller 840 may generate the first control signal f_syn by synthesizing the first reference signal f_c having the frequency component of the measurement signal and the second reference signal f_ch_in having the predetermined frequency component included in the frequency bandwidth of the amplifier 850.

In a second measurement mode for measuring biopotential information, the controller 840 generates a first control signal based on the second reference signal f_ch_in and a first reference signal having a fixed signal level, such as a reference voltage, instead of using the first reference signal f_c. The reference voltage is in a high logic state at all times regardless of time. Accordingly, when the controller 840 performs an XNOR logic operation on the reference voltage corresponding to the first reference signal and the second reference signal, the first control signal generated by the controller 840 may have the same frequency component as the second reference signal f_ch_in.

The first converter 830 modulates a frequency component of a biosignal transferred from the interface 820, based on the first control signal received from the controller 840. The first converter 830 may include a chopper of which a switching operation is controlled based on the first control signal. The first converter 830 modulates the frequency component of the input biosignal by adjusting a connection relationship between switches included in the chopper based on the first control signal. The biosignal transferred from the interface 820 is modulated to a signal of which a frequency component is included in the frequency bandwidth of the amplifier 850 through the switching operation of the first converter 830.

Although the frequency component of the biosignal transferred from the interface 820 is outside the frequency bandwidth of the amplifier 850, the biosignal may be modulated by the first converter 830 so that the frequency component of the biosignal may be included in the frequency bandwidth of the amplifier 850. The first converter 830 may transfer, to the amplifier 850, the biosignal of which the frequency component is modulated.

The amplifier 850 receives, from the first converter 830, the biosignal of which the frequency component is modulated, and amplifies the received biosignal. The biosignal amplified by the amplifier 850 is demodulated to a signal of a baseband by the second converter 860. The second converter 860 may include a chopper of which a switching operation is controlled based on the second control signal. The second converter 860 demodulates the frequency component of the input signal to the signal of the baseband by adjusting a connection relationship between switches included in the chopper based on the second control signal.

A frequency component or an operation clock of the second control signal f_ch_out may be equal to the second reference signal f_ch_in input to the controller 840, or may have a phase difference of 90 degrees with the second reference signal f_ch_in. When the frequency component of the second control signal f_ch_out is equal to the frequency component of the second reference signal f_ch_in, a real number component of the biosignal is included in an output signal of the second converter 860. When the frequency component of the second control signal f_ch_out has a phase difference of 90 degrees with the frequency component of the second reference signal f_ch_in, an imaginary number component of the biosignal is included in the output signal of the second converter 860.

For example, when the biosignal is in a form of an AC voltage, the first converter 830 may output AC voltages V_IA_ip and V_IA_in having the modulated frequency component to two terminals of the amplifier 850, respectively. The AC voltages V_IA_ip and V_IA_in input to the amplifier 850 may be amplified by the amplifier 850. The second converter 860 may output AC voltages V_IA_op and V_IA_on that are demodulated to a signal of a baseband. To avoid a low frequency noise band of the amplifier 850, the first converter 830 may modulate the input biosignal to a signal of an intermediate frequency band greater than the low frequency noise band of the amplifier 850 and included in the frequency bandwidth of the amplifier 850, without modulating the input biosignal to the signal of the baseband. The second converter 860 may convert, to the signal of the baseband, the biosignal modulated to the signal of the intermediate frequency band and amplified.

Figure 9:
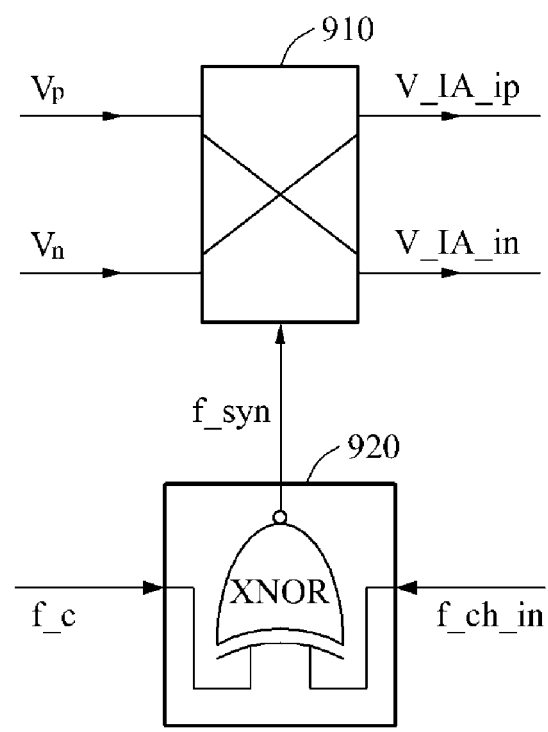
FIG. 9 is a circuit diagram illustrating an example of a operation method of a controller.

FIG. 9 illustrates a circuit diagram that describes an example of a method of operating a controller 920.

The controller 920 generates a first control signal for controlling a first converter 910. The controller 920 generates a first control signal f_syn having a synthetic frequency component based on a first reference signal f_c having a frequency component of a measurement signal and a second reference signal f_ch_in having a predetermined frequency component included in a frequency bandwidth of an amplifier. The controller 920 generates the first control signal f_syn by performing an XNOR logic operation on the first reference signal f_c and the second reference signal f_ch_in. For example, when all of the first reference signal f_c and the second reference signal f_ch_in input to the controller 920 are in a high logic state or a low logic state, the first control signal f_syn generated through the XNOR logic operation may have the high logic state. When the first reference signal f_c and the second reference signal f_ch_in input to the controller 920 are in different logic states, the first control signal f_syn generated through the XNOR logic operation may have the low logic state. The first converter 910 may modulate frequency components of first signals $V_p$ and $V_n$ that are input signals based on the first control signal f_syn output from the controller 920, and may output the modulated signals V_IA_ip and V_IA_in as second signals.

Figure 10:
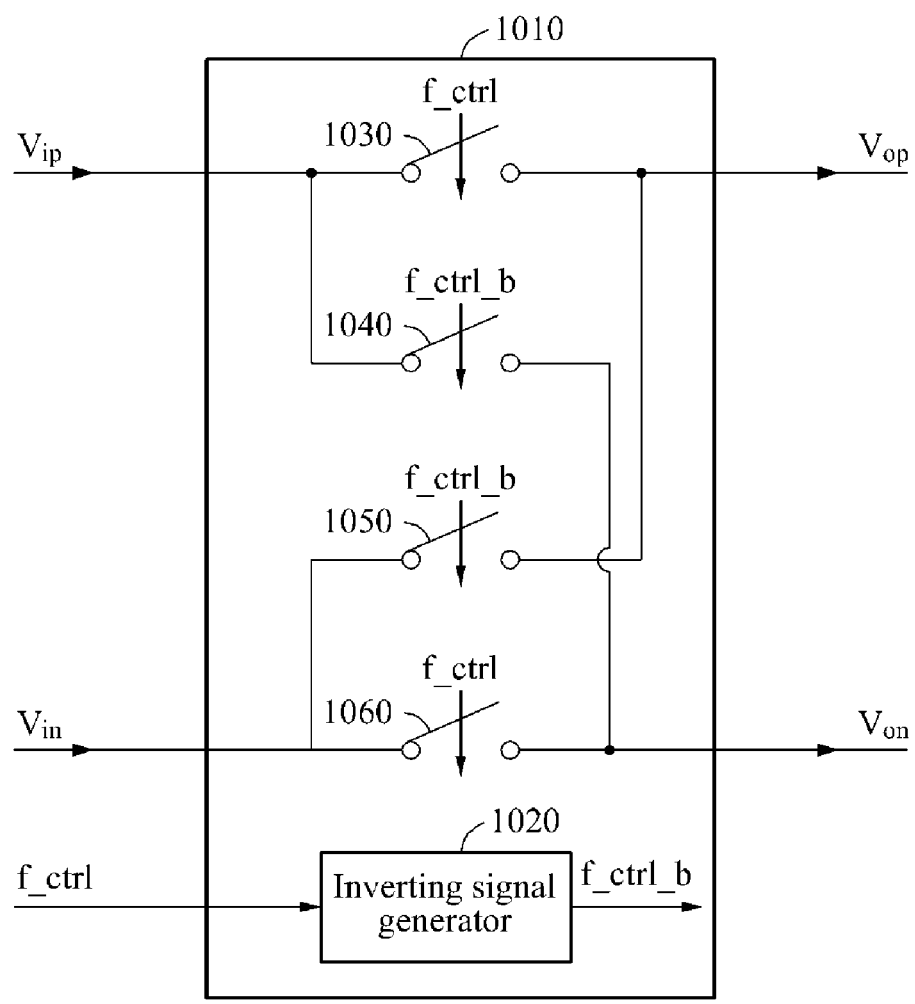
FIG. 10 is a circuit diagram illustrating an example of a operation method of a first converter and a second converter.

FIG. 10 illustrates a circuit diagram describing an example of a method of operating a first converter and a second converter.

A converter 1010 of the first converter or the second converter includes a chopper having its switching operation controlled based on a control signal. The converter 1010 includes analog switches 1030, 1040, 1050, and 1060, and an inverting signal generator 1020. The inverting signal generator 1020 receives a control signal f_ctrl and generates a non-overlapping inverting signal f_ctrl_b based on the control signal f_ctrl. The inverting signal generator 1020 may generate and output an inverting signal of an input signal, and may generate an output signal so that a high logic state may not temporally overlap between the input signal and the output signal. The analog switches 1030 and 1060 may be controlled based on the control signal f_ctrl input to the converter 1010, and the analog switches 1040 and 1050 may be controlled based on the output signal f_ctrl_b of the inverting signal generator 1020.

Figure 11:
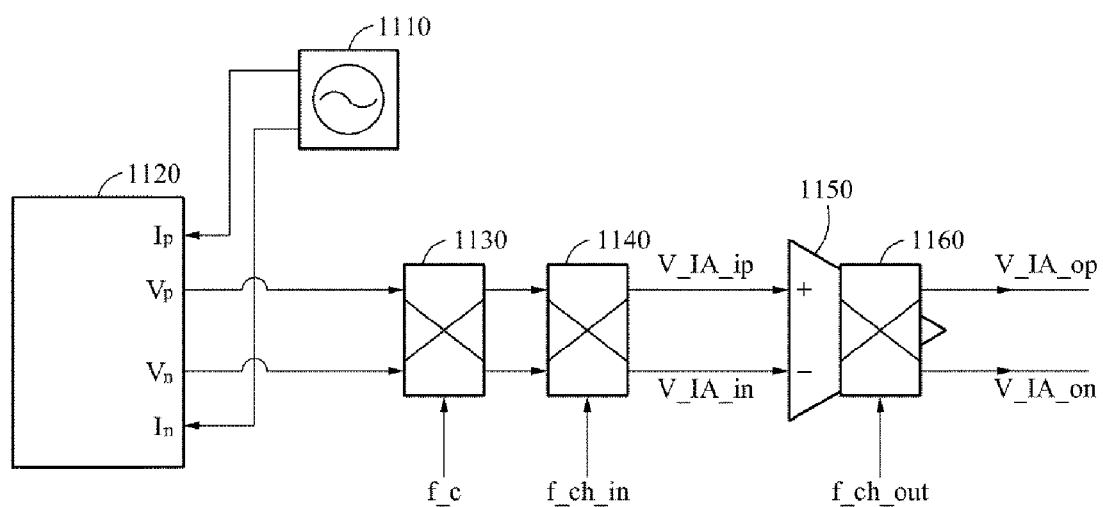
FIG. 11 is a circuit diagram illustrating another example of a signal processing apparatus.

FIG. 11 illustrates a circuit diagram of an example of a signal processing apparatus. A measurement signal generator 1110, an interface 1120, an amplifier 1150, and a second converter 1160 of FIG. 11 correspond to the measurement signal generator 810, the interface 820, the amplifier 850, and the second converter 860 of FIG. 8, respectively. Accordingly, a further description related thereto will be omitted here.

The first converter 830 may correspond to a first sub-converter 1130 and a second sub-converter 1140 in terms of functions. In an example, the first converter 830 may include the first sub-converter 1130 and the second sub-converter 1140 connected to the first sub-converter 1130. The first sub-converter 1130 and the second sub-converter 1140 may include a chopper of which a switching operation is controlled based on a control signal.

The first sub-converter 1130 converts a biosignal transferred from the interface 1120 to a signal of a baseband, based on a first reference signal f_c having a frequency component of a measurement signal generated by the measurement signal generator 1110. The biosignal converted to the signal of the baseband by the first sub-converter 1130 is transferred to the second sub-converter 1140. The second sub-converter 1140 converts the biosignal converted to the signal of the baseband to a signal having a frequency component included in a frequency bandwidth of the amplifier 1150 based on a predetermined second reference signal f_ch_in included in the frequency bandwidth of the amplifier 1150. In FIG. 8, using a first control signal synthesized by the controller 840 and the first converter 830, a frequency component of a biosignal may be modulated to a frequency component included in the frequency bandwidth of the amplifier 850. In FIG. 11, instead of using a first control signal, a frequency component of a biosignal may be modulated to a frequency component included in the frequency bandwidth of the amplifier 1150 through a sequential frequency component modulation process including two operations using the first sub-converter 1130 and the second sub-converter 1140.

In general, a frequency modulation of an input signal using the chopper may be performed based on a control signal having a constant duty ratio as illustrated in the first sub-converter 1130 and the second sub-converter 1140 of FIG. 11. In FIG. 8, the frequency modulation performed by the first converter 830 may be performed based on a control signal in which signal components having different duty ratios are repeatedly present.

FIGS. 12A through 12E illustrate waveforms of examples of signal input and output in a first measurement mode.

Figure 12A:
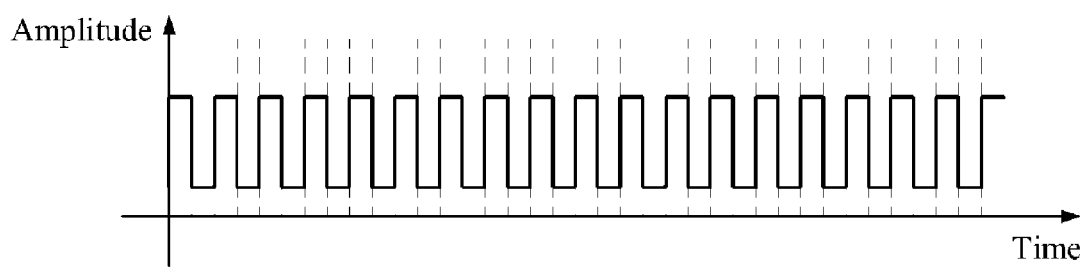
FIGS. 12A through 12E are waveforms illustrating examples of signal input and output in a first measurement mode.
Figure 12B:
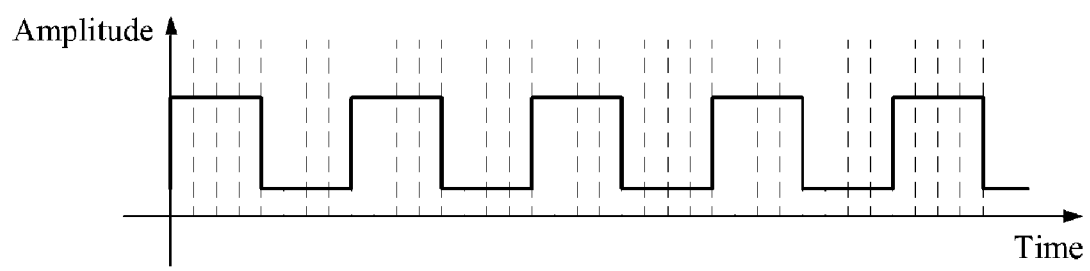

FIG. 12A shows a frequency component of a measurement signal as a first reference signal f_c input to the controller 330. FIG. 12B shows a predetermined frequency component included in the frequency bandwidth of the amplifier 340 as a second reference signal f_ch_in input to the controller 330.

Figure 12C:
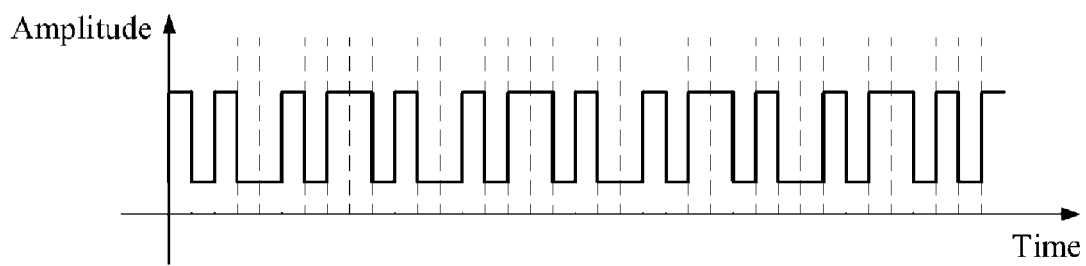

FIG. 12C shows a first control signal f_syn generated by the controller 330 based on the first reference signal f_c and the second reference signal f_ch_in. In an example, the controller 330 may synthesize the first control signal f_syn by performing an XNOR logic operation on the first reference signal f_c and the second reference signal f_ch_in. For example, when all of the first reference signal f_c and the second reference signal f_ch_in are in a high logic state at the same time, the first control signal f_syn may have a high logic value. When the first reference signal f_c and the second reference signal f_ch_in are in different logic states at the same time, the first control signal f_syn may have a low logic value.

Figure 12D:
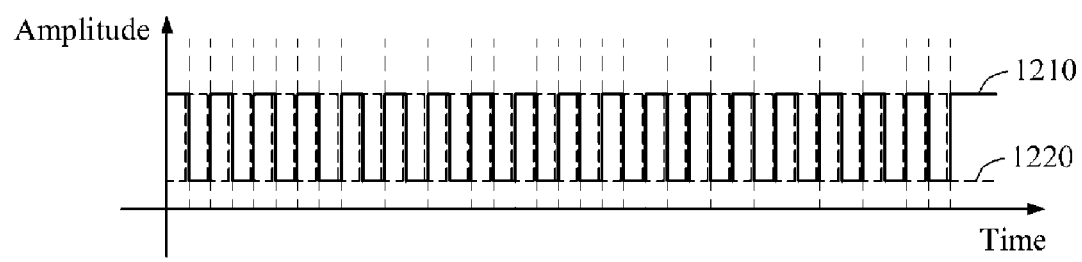

FIG. 12D shows first signals $V_p$ 1210 and $V_n$ 1220 input to the first converter 320. The first signals $V_p$ 1210 and $V_n$ 1220 have a phase difference of 180 degrees. For example, the first signals $V_p$ 1210 and $V_n$ 1220 may be biosignals measured through a bio-electrode and may have a form in an AC voltage.

Figure 12E:
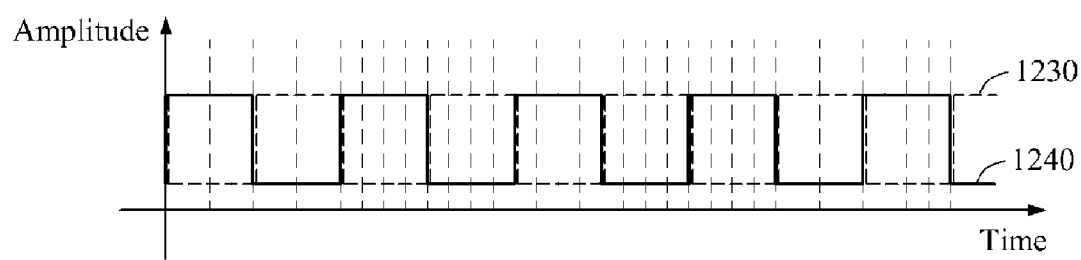

FIG. 12E shows second signals V_IA_ip 1240 and V_IA_in 1230 output from the first converter 320. The second signals V_IA_ip 1240 and V_IA_in 1230 have a phase difference of 180 degrees. The first converter 320 may convert the first signals $V_p$ 1210 and $V_n$ 1220 to the second signals V_IA_ip 1240 and V_IA_in 1230 that are signals of a low frequency band. The first converter 320 may convert the first signals $V_p$ 1210 and $V_n$ 1220 that are signals of a high frequency band to the second signals V_IA_ip 1240 and V_IA_in 1230 having the frequency component included in the frequency bandwidth of the amplifier 340. The first converter 320 may modulate the frequency components of the first signals $V_p$ 1210 and $V_n$ 1220 shown in FIG. 12D, based on the first control signal f_syn shown in FIG. 12C. Accordingly, the second signals V_IA_ip 1240 and V_IA_in 1230 modulated to the signal of the low frequency band may be generated as shown in FIG. 12E.

Figure 13:
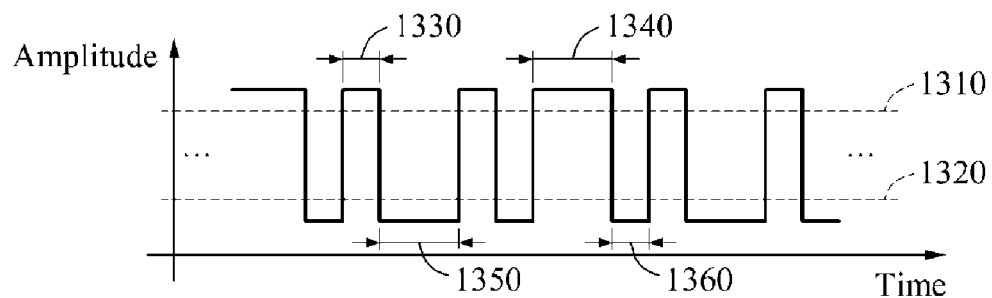
FIG. 13 is a waveform illustrating an example of a first control signal.

FIG. 13 illustrates an example of a waveform of a first control signal or a second control signal.

In a first measurement mode, the controller 220 generates the first control signal based on a first reference signal and a second reference signal. The first control signal has a first time width 1330 and a second time width 1340 that are different time intervals in which a signal amplitude is greater than an upper threshold value 1310, and has a third time width 1350 and a fourth time width 1360 that are different time intervals in which the signal amplitude is less than a lower threshold value 1320. The first time width 1330 is equal to the fourth time width 1360 and the second time width 1340 is equal to the third time width 1350.

In a fourth measurement mode, the controller 220 generates the second control signal based on a control signal for controlling the measurement signal generator 210 and the first control signal. For example, the controller 220 may generate the second control signal by performing an XNOR logic operation on the first control signal and the control signal for controlling the measurement signal generator 210, or by performing an XNOR logic operation on the first control signal and a phase-shifted signal of the control signal for controlling the measurement signal generator 210. In the fourth measurement mode, the second control signal generated by the controller 220 may show the same signal waveform as shown in FIG. 13. The second control signal has the first time width 1330 and the second time width 1340 that are different time intervals in which the signal amplitude is greater than the upper threshold value 1310, and has the third time width 1350 and the fourth time width 1360 that are different time intervals in which the signal amplitude is less than the lower threshold value 1320. The first time width 1330 is equal to the fourth time width 1360 and the second time width 1340 is equal to the third time width 1350.

FIGS. 14A through 14E illustrate examples of a signal input or output in a fourth measurement mode.

Figure 14A:
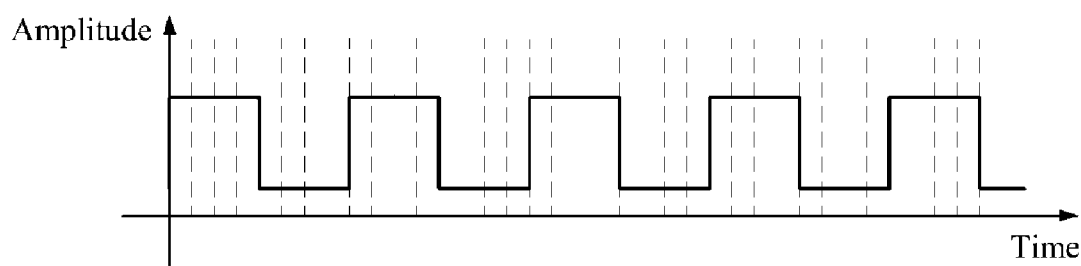
FIGS. 14A through 14E are waveforms illustrating examples of signal input and output in a fourth measurement mode.
Figure 14B:
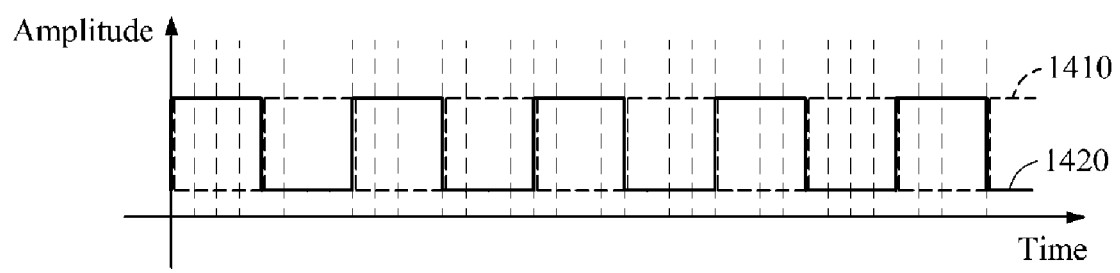
Figure 14C:
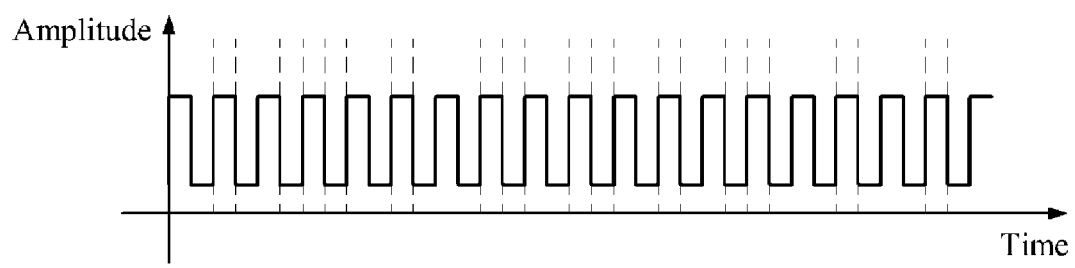

FIG. 14A shows a control signal for controlling the measurement signal generator 210. FIG. 14B shows biosignals 1410 and 1420 input to the first converter 230. The biosignals 1410 and 1420 input to the first converter 230 have a phase difference of 180 degrees. FIG. 14C shows a first control signal for controlling the first converter 230. The first converter 230 may convert a biosignal to a signal included in the amplifiable frequency band of the amplifier 240 and capable of avoiding the low frequency noise band of the amplifier 240 based on the first control signal.

Figure 14D:
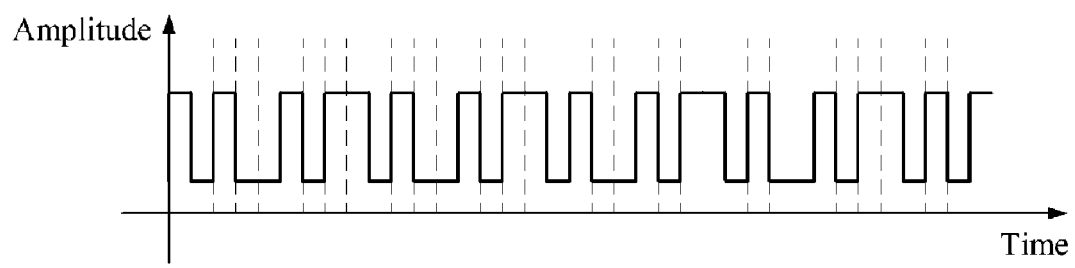
Figure 14E:
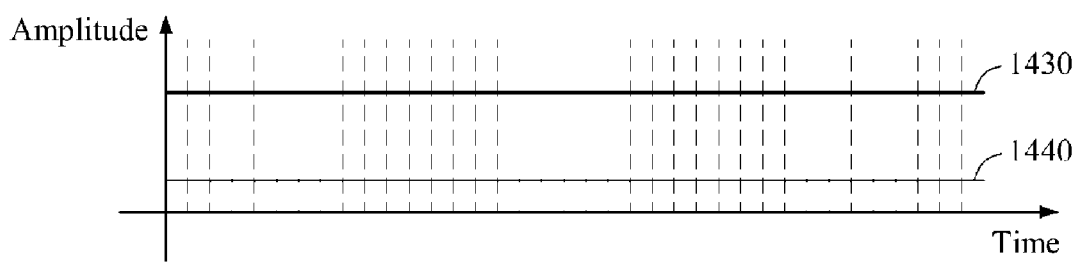

FIG. 14D shows a second control signal for controlling the second converter 250. The second control signal may be generated based on the first control signal and the control signal for controlling the measurement signal generator 210. In an example, the controller 220 may generate the second control signal by performing an XNOR logic operation on the first control signal and the control signal for controlling the measurement signal generator 210. In another example, the controller 220 may generate the second control signal by performing an XNOR logic operation on the first control signal and a phase-shifted signal of the control signal for controlling the measurement signal generator 210. The second control signal may have a first time width or a second time width that is a time interval in which a signal amplitude is greater than an upper threshold value, and may have a third time width or a fourth time width that is a time interval in which the signal amplitude is less than a lower threshold value. FIG. 14E shows output signals 1430 and 1440 of the second converter 250.

Figure 15:
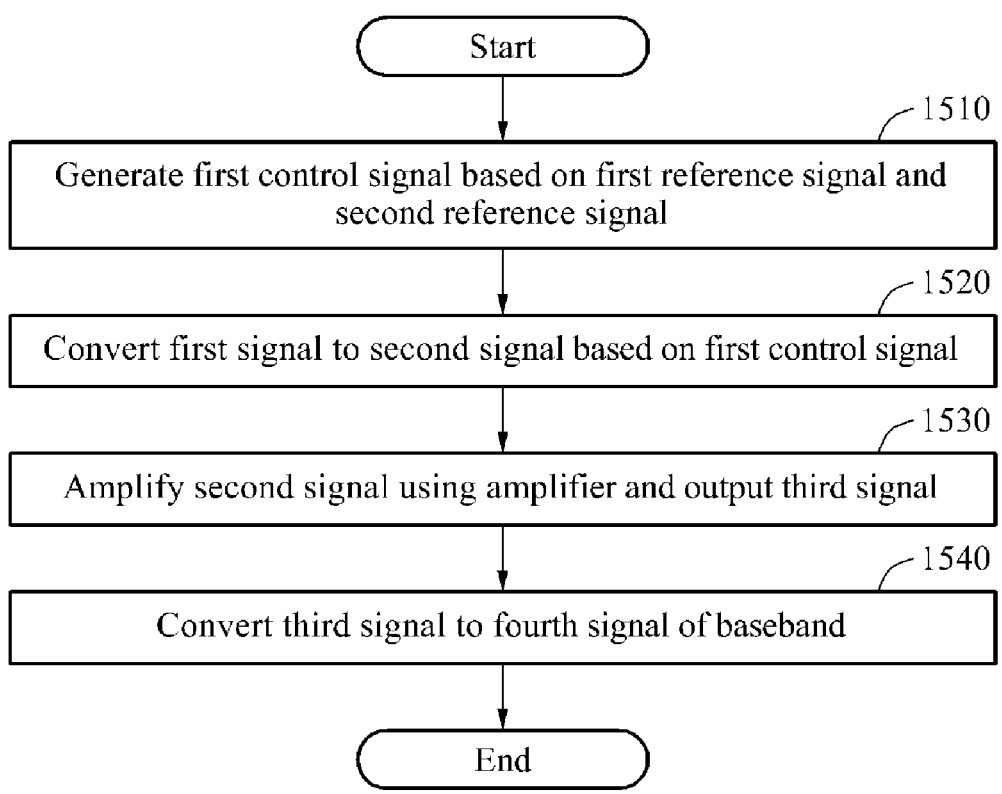
FIG. 15 is a flowchart illustrating an example of a signal processing method.

FIG. 15 illustrates an example of a signal processing method.

In operation 1510, a signal processing apparatus generates a first control signal based on a first reference signal having a frequency component of a measurement signal and a second reference signal having a predetermined frequency component included in a frequency bandwidth of an amplifier. For example, the signal processing apparatus may generate the first control signal by performing an XNOR logic operation on the first reference signal and the second reference signal.

In operation 1520, the signal processing apparatus converts a first signal to a second signal based on the generated first control signal. The signal processing apparatus may convert the first signal having a frequency component located outside the frequency bandwidth of the amplifier to the second signal having the frequency component included in the frequency bandwidth of the amplifier. The signal processing apparatus may convert the first signal to the second signal having the frequency component included in the frequency bandwidth of the amplifier and greater than a low frequency band area of the amplifier. The signal processing apparatus may modulate the frequency component of the first signal by controlling a chopper to which the first signal is input, based on the first control signal.

In operation 1530, the signal processing apparatus amplifies the second signal using the amplifier and outputs a third signal. The signal processing apparatus may amplify the second signal input to the amplifier based on a gain of the amplifier, and may generate the third signal.

In operation 1540, the signal processing apparatus converts the third signal to a fourth signal of a baseband. The signal processing apparatus may generate the second control signal for controlling the second converter, and may convert the third signal to the fourth signal based on the second control signal. The signal processing apparatus may change a frequency component of the third signal based on the second control signal that is determined based on the second reference signal. The signal processing apparatus may demodulate the third signal by controlling a chopper to which the third signal is input based on the second control signal, and may generate the fourth signal having the frequency component of the baseband.

The second control signal may be a signal having the same frequency component as the second reference signal or may be a signal having a phase difference of 90 degrees with the second reference signal. When the frequency component of the second control signal is equal to the frequency component of the second reference signal, the fourth signal may include a real number component. When the second control signal has a phase difference of 90 degrees with the second reference signal, the fourth signal may include an imaginary number component.

Figure 16:
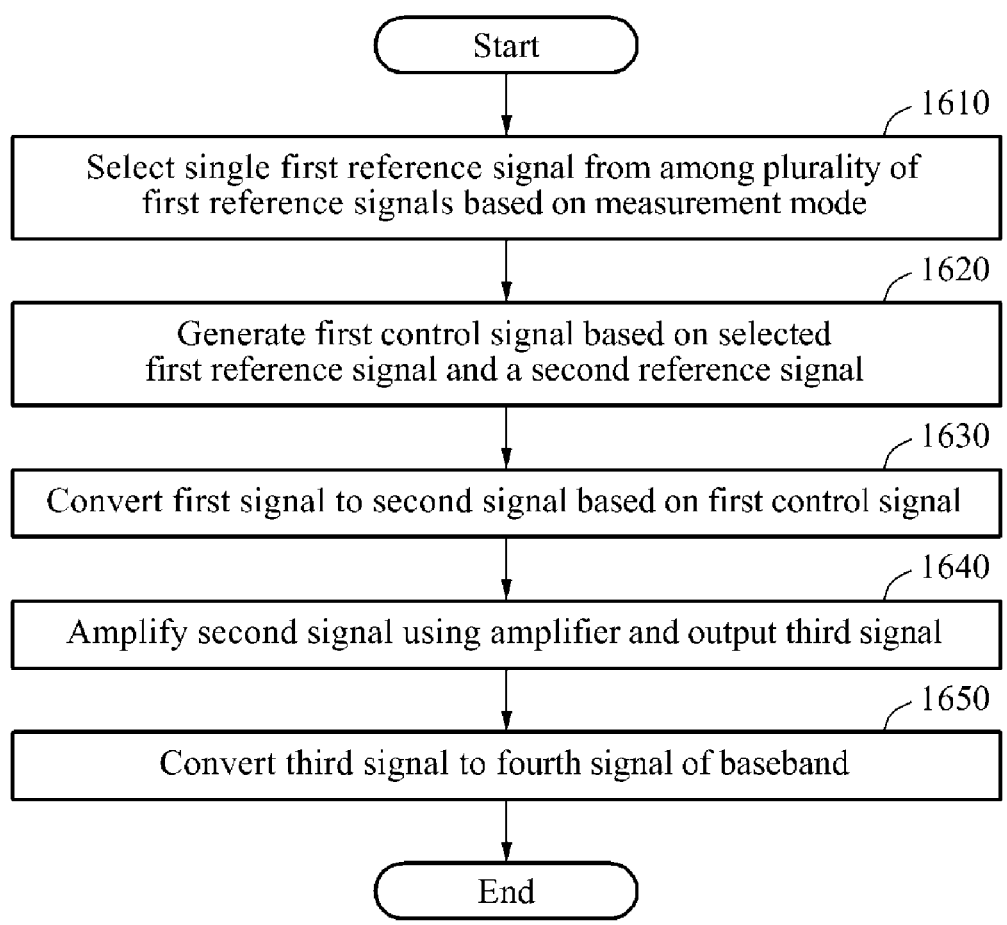
FIG. 16 is a flowchart illustrating another example of a signal processing method.

FIG. 16 illustrates another example of a signal processing method.

In operation 1610, a signal processing apparatus selects a single first reference signal from among a plurality of first reference signals based on a measurement mode. In a first measurement mode for measuring bio-impedance information, the signal processing apparatus may select a signal having a frequency component of a measurement signal as the first reference signal. In a second measurement mode for measuring biopotential information, the signal processing apparatus may select a signal having a fixed signal level over time as the first reference signal.

In operation 1620, the signal processing apparatus generates a first control signal based on the selected first reference signal and a second reference signal. For example, the signal processing apparatus may generate the first control signal by performing an XNOR logic operation on the first reference signal and the second reference signal. In the first measurement mode, the first control signal may be generated by performing an XNOR logic operation on the signal having the frequency component of the measurement signal and a signal having a predetermined frequency component included in a frequency bandwidth of an amplifier. In the second measurement mode, the first control signal may be generated by performing an XNOR logic operation on a signal having a fixed signal level over time and the signal having the predetermined frequency component included in the frequency bandwidth of the amplifier.

In operation 1630, the signal processing apparatus converts a first signal corresponding to an input signal to a second signal based on the first control signal. The signal processing apparatus may modulate a frequency component of the first signal using a chopper of which a switching operation is controlled based on the first control signal, and may generate the second signal.

In operation 1640, the signal processing apparatus amplifies the second signal using the amplifier and outputs the third signal. The signal processing apparatus may amplify the second signal input to the amplifier based on a gain of the amplifier, and may generate the third signal.

In operation 1650, the signal processing apparatus converts the third signal to a fourth signal of a baseband. The signal processing apparatus may generate the second control signal for controlling the second converter, and may convert the third signal to the fourth signal based on the second control signal. The signal processing apparatus may demodulate a frequency component of the third signal using the chopper of which the switching operation is controlled based on the second control signal, and may generate the fourth signal having the frequency component of the baseband.

The second control signal may be a signal having the same frequency component as the second reference signal, or may be a signal having a phase difference of 90 degrees with the second reference signal. When the frequency component of the second control signal is equal to the frequency component of the second reference signal, the fourth signal may include a real number component. When the second control signal has a phase difference of 90 degrees with the second reference signal, the fourth signal may include an imaginary number component.

Figure 17:
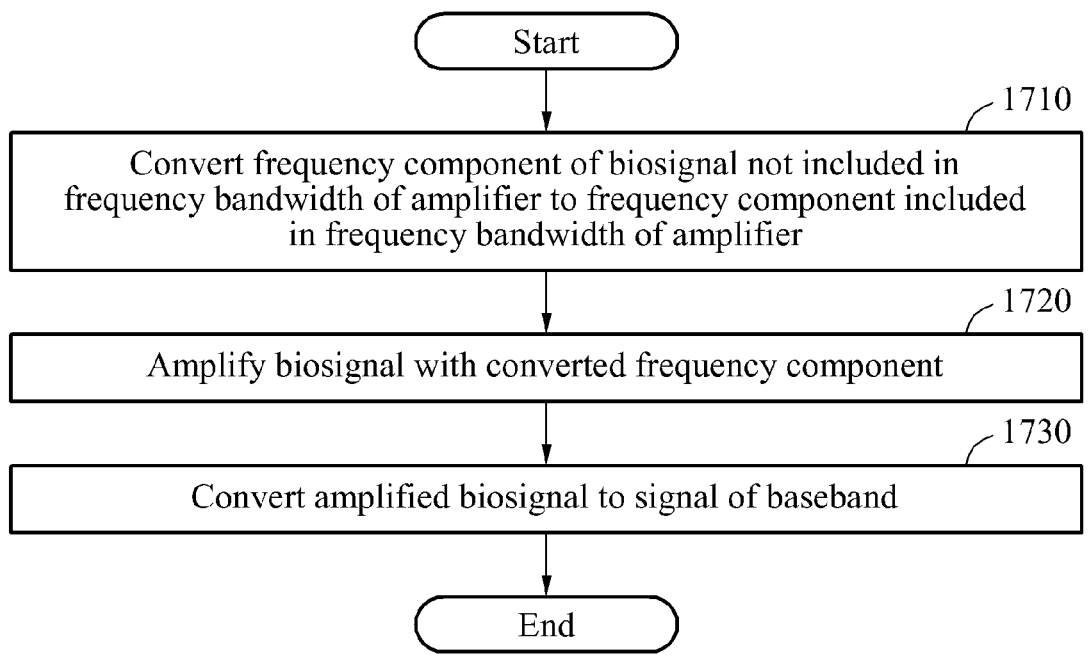
FIG. 17 is a flowchart illustrating an example of a biosignal processing method.

FIG. 17 illustrates an example of a biosignal processing method.

In operation 1710, a biosignal processing apparatus converts a frequency component of a biosignal not included in a frequency bandwidth of an amplifier to a frequency component included in the frequency bandwidth of the amplifier. For example, when the frequency component of the biosignal measured from a bio-electrode is outside the frequency bandwidth of the amplifier, the biosignal processing apparatus may convert the biosignal to a signal having a frequency component included in the frequency bandwidth of the amplifier and greater than a low frequency band of the amplifier.

The converted frequency component of the biosignal may be less than or greater than the frequency component of the biosignal measured from a subject. Also, the frequency component of the biosignal may be greater than a frequency component of a baseband signal.

In operation 1720, the biosignal processing apparatus amplifies the biosignal of which the frequency component is converted. In operation 1710, the biosignal is converted to the signal having the frequency component included in the amplifiable frequency bandwidth of the amplifier, and the amplifier of the biosignal processing apparatus may normally amplify the biosignal of which the frequency component is converted.

In operation 1730, the biosignal processing apparatus converts the amplified biosignal to a signal of a baseband. For example, the biosignal processing apparatus may convert the amplified biosignal to the signal having the frequency component of the baseband using a chopper of which a switching operation is controlled based on a control signal. A real number component or an imaginary number component may be demodulated from the biosignal amplified based on the control signal.

The units described herein may be implemented using hardware components and software components. For example, the hardware components may include microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as floptical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of processing signal, the method comprising:
receiving a first reference signal having a frequency component of a measurement signal to be applied to a subject;
receiving a second reference signal having a frequency component within a frequency bandwidth of an amplifier; and
converting a first signal measured from the subject to a second signal within the frequency bandwidth of the amplifier, based on the first reference signal and the second reference signal,
wherein the converting comprises:
generating a first control signal by combining the first reference signal and the second reference signal; and
converting the first signal to the second signal based on the first control signal.

2. The method of claim 1, wherein the generating comprises generating the first control signal by performing an XNOR logic operation on the first reference signal and the second reference signal.

3. The method of claim 1, wherein the first control signal has a first time width and a second time width in which a signal amplitude is greater than an upper threshold value, and has a third time width and a fourth time width in which the signal amplitude is less than a lower threshold value.

4. The method of claim 3, wherein the first time width is equal to the fourth time width, and
the second time width is equal to the third time width.

5. The method of claim 1, the method further comprising:
generating a third signal by amplifying the second signal using the amplifier; and
converting the third signal to a fourth signal of a baseband.

6. The method of claim 5, wherein the converting of the third signal to the fourth signal comprises:
converting the third signal to the fourth signal based on a second control signal having a frequency component equal to the frequency component of the second reference signal.

7. The method of claim 5, wherein the converting of the third signal to the fourth signal comprises:
converting the third signal to the fourth signal based on a second control signal acquired by phase-shifting the second reference signal by 90 degrees.

8. The method of claim 1, wherein the first signal has a frequency component outside the range of the frequency bandwidth of the amplifier, and
the second signal has an intermediate frequency component within a frequency bandwidth range of the amplifier.

9. A method of processing signal, the method comprising:
selecting a single first reference signal from among a plurality of first reference signals based on a measurement mode;
generating a first control signal based on the selected first reference signal and a second reference signal having a frequency component within a frequency bandwidth of an amplifier; and
converting a first signal measured from a subject to a second signal within the frequency bandwidth of the amplifier, based on the first control signal.

10. The method of claim 9, wherein the selecting comprises selecting a first reference signal having a frequency component of a measurement signal to be applied to the subject in a first measurement mode, and selecting a first reference signal having a fixed signal level over time in a second measurement mode.

11. The method of claim 10, wherein the first measurement mode is a mode for measuring bio-impedance information, and the second measurement mode is a mode for measuring biopotential information.

12. The method of claim 9, wherein the generating comprises generating the first signal by performing an XNOR logic operation on the first reference signal and the second reference signal.

13. The method of claim 9, wherein the first control signal has a first time width and a second time width in which a signal amplitude is greater than an upper threshold value, and has a third time width and a fourth time width in which the signal amplitude is less than a lower threshold value.

14. The method of claim 9, the method further comprising:
generating a third signal by amplifying the second signal using the amplifier; and
converting the third signal to a fourth signal of a baseband.

15. A signal processing apparatus comprising:
a controller configured to generate a first control signal based on a first reference signal having a frequency component of a measurement signal and a second reference signal having a predetermined frequency component within a frequency bandwidth of an amplifier;
a first converter configured to convert a first signal to a second signal having a frequency component within the frequency bandwidth of the amplifier, based on the first control signal;
the amplifier configured to output a third signal by amplifying the second signal; and
a second converter configured to convert the third signal to a fourth signal of a baseband,
wherein the controller is configured to generate the first control signal by performing an XNOR logic operation on the first reference signal and the second reference signal.

16. A signal processing apparatus comprising:
a controller configured to generate a first control signal based on a first reference signal having a frequency component of a measurement signal and a second reference signal having a predetermined frequency component within a frequency bandwidth of an amplifier;
a first converter configured to convert a first signal to a second signal having a frequency component within the frequency bandwidth of the amplifier, based on the first control signal;
the amplifier configured to output a third signal by amplifying the second signal; and
a second converter configured to convert the third signal to a fourth signal of a baseband wherein the first control signal has a first time width and a second time width in which a signal amplitude is greater than an upper threshold value, and has a third time width and a fourth time width in which the signal amplitude is less than a lower threshold value.

17. The apparatus of claim 15, wherein the second converter is configured to convert the third signal to the fourth signal based on a second control signal having a frequency component equal to the frequency component of the second reference signal.

18. A signal processing apparatus comprising:
a controller configured to generate a first control signal based on first reference signal having a frequency component of a measurement signal and a second reference signal having a predetermined frequency component with a frequency bandwidth of amplifier;
the amplifier configured to output a third signal by simplifying the second signal; and
a second converter configured to convert the third signal to a fourth signal of a baseband, wherein the second converter is configured to convert the third signal to the fourth signal based on a second control signal acquired by phase-shifting the second reference signal by 90 degrees.

19. The apparatus of claim 15, wherein the signal processing apparatus is comprised in and operates within a wearable device.

20. A biosignal processing apparatus comprising:
a first converter configured to convert a frequency component of a biosignal outside a frequency bandwidth of an amplifier to a frequency component within the frequency bandwidth of the amplifier;
the amplifier configured to amplify the biosignal having the frequency component converted; and
a controller configured to generate a first control signal based on a first reference signal having a frequency component of a measurement signal and a second reference signal having a predetermined frequency component comprised in the frequency bandwidth of the amplifier, wherein the controller is configured to generate the first control signal by performing and XNOR logic operation on the first reference signal and the second reference signal.

21. The apparatus of claim 20, wherein the converted frequency component of the biosignal is less than a frequency component of a biosignal measured from a subject.

22. The apparatus of claim 20, wherein the converted frequency component of the biosignal is greater than a frequency component of a biosignal measured from a subject.

23. The apparatus of claim 21, wherein the converted frequency component of the biosignal is greater than a frequency component of a baseband signal.

24. The apparatus of claim 20, the apparatus further comprising:
a second converter configured to convert the amplified biosignal to a signal of a baseband.

25. The apparatus of claim 20, wherein the first control signal has a first time width and a second time width in which a signal amplitude is greater than an upper threshold value, and has a third time width and a fourth time width in which the signal amplitude is less than a lower threshold value.

26. An apparatus comprising:
an interface configured to transmit a measurement signal to a subject and to receive a reaction signal from the subject;
a first converter configured to, in response to a frequency component of a first signal based on the received reaction signal being outside of a frequency bandwidth of an amplifier, convert the first signal to a second signal having a frequency component within the frequency bandwidth of the amplifier;
the amplifier configured to amplify the second signal; and
a controller configured to generate a first control signal based on a first reference signal having a frequency component of the measurement signal and a second reference signal having a frequency component within the frequency bandwidth of the amplifier, the first converter being configured to convert the first signal to the second signal based on the first control signal,
wherein the controller is configured to generate the first control signal by performing an XNOR logic operation on the first reference signal and the second reference signal.

* * * * *